(12) United States Patent
Kamalakshakurup et al.

(10) Patent No.: US 10,780,438 B2
(45) Date of Patent: Sep. 22, 2020

(54) HIGH-EFFICIENCY ENCAPSULATION IN DROPLETS BASED ON HYDRODYNAMIC VORTICES CONTROL

(71) Applicant: The Regents of the University of California, Oakland, CA (US)

(72) Inventors: Gopakumar Kamalakshakurup, Irvine, CA (US); Abraham P. Lee, Irvine, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 221 days.

(21) Appl. No.: 16/005,533

(22) Filed: Jun. 11, 2018

(65) Prior Publication Data
US 2018/0353963 A1 Dec. 13, 2018

Related U.S. Application Data

(60) Provisional application No. 62/517,797, filed on Jun. 9, 2017.

(51) Int. Cl.
*G01N 35/08* (2006.01)
*G01N 15/06* (2006.01)
(Continued)

(52) U.S. Cl.
CPC ... *B01L 3/502784* (2013.01); *B01L 3/502746* (2013.01); *B01L 3/502761* (2013.01);
(Continued)

(58) Field of Classification Search
CPC ........ G01N 35/08; G01N 15/06; G01N 33/00; G01N 33/48; G01N 35/00; G01N 1/286;
(Continued)

(56) References Cited

U.S. PATENT DOCUMENTS

| 2,656,508 A | 10/1953 | Coulter |
| 3,380,584 A | 4/1968 | Fulwyler |

(Continued)

FOREIGN PATENT DOCUMENTS

| GB | 2395196 | 5/2004 |
| WO | WO2007120240 A2 | 10/2007 |

(Continued)

OTHER PUBLICATIONS

International Search Report for PCT Application No. PCT/US17/55984 dated Dec. 14, 2017.
(Continued)

*Primary Examiner* — Brian J. Sines
(74) *Attorney, Agent, or Firm* — Nguyen Tarbet

(57) ABSTRACT

An interfacial technique utilizes hydrodynamic micro-vortices to perform (i) high efficiency single cell encapsulation and (ii) size-selective capturing of cells based on their sizes in a single microfluidic device. A notable feature of this technique is that it can perform high efficiency single cell encapsulation at low cell concentrations, and this technique is all passive, controlled only by the flow rates of the two phases and does not require complex structures or on-chip active devices. Single bead/cell encapsulation was demonstrated at 50% efficiency, which is at least 10 times greater than the random encapsulations at the introduced cell concentrations. Also demonstrated is the selective trapping of cells based on their sizes. This present technique expands the capabilities of droplet microfluidics for applications ranging from single cell genomics, proteomic assays to sample preparation.

20 Claims, 12 Drawing Sheets

(51) Int. Cl.

| | | |
|---|---|---|
| G01N 33/00 | (2006.01) | |
| G01N 33/48 | (2006.01) | |
| G01N 35/00 | (2006.01) | |
| B01L 3/00 | (2006.01) | |
| G01N 1/28 | (2006.01) | |
| A61B 5/15 | (2006.01) | |
| G01N 15/10 | (2006.01) | |
| G01N 15/00 | (2006.01) | |
| G01N 15/02 | (2006.01) | |

(52) U.S. Cl.
CPC ............ *G01N 1/286* (2013.01); *A61B 5/1405* (2013.01); *B01L 2200/0636* (2013.01); *B01L 2200/141* (2013.01); *B01L 2200/143* (2013.01); *B01L 2300/0867* (2013.01); *B01L 2400/022* (2013.01); *G01N 15/0255* (2013.01); *G01N 2015/0053* (2013.01); *G01N 2015/1006* (2013.01)

(58) Field of Classification Search
CPC ...... B01L 3/502; B01L 3/00; B01L 3/502784; B01L 3/502746; B01L 3/502761
See application file for complete search history.

(56) References Cited

U.S. PATENT DOCUMENTS

| | | | |
|---|---|---|---|
| 4,009,435 | A | 2/1977 | Hogg |
| 5,465,582 | A | 11/1995 | Bliss et al. |
| 8,263,023 | B2 | 9/2012 | Le Vot et al. |
| 8,365,311 | B2 | 1/2013 | Nawarathna |
| 8,927,040 | B2 | 1/2015 | Brand et al. |
| 2002/0182654 | A1 | 12/2002 | Jing et al. |
| 2004/0234588 | A1 | 11/2004 | Lu et al. |
| 2005/0015001 | A1 | 1/2005 | Lec et al. |
| 2005/0106064 | A1 | 5/2005 | Laurell et al. |
| 2005/0272039 | A1 | 12/2005 | Yasuda |
| 2005/0272096 | A1 | 12/2005 | Clague et al. |
| 2006/0051329 | A1 | 3/2006 | Lee et al. |
| 2006/0177815 | A1 | 8/2006 | Soh et al. |
| 2007/0264320 | A1 | 11/2007 | Lee et al. |
| 2008/0038807 | A1 | 2/2008 | Pommersheim |
| 2008/0241875 | A1 | 10/2008 | Hwang et al. |
| 2009/0042310 | A1 | 2/2009 | Ward et al. |
| 2009/0068170 | A1 | 3/2009 | Weitz et al. |
| 2009/0075390 | A1 | 3/2009 | Linder et al. |
| 2009/0286300 | A1 | 11/2009 | Le Vot et al. |
| 2009/0298191 | A1 | 12/2009 | Whitesides et al. |
| 2011/0059556 | A1 | 3/2011 | Strey et al. |
| 2011/0086352 | A1 | 4/2011 | Bashir et al. |
| 2012/0034155 | A1 | 2/2012 | Hyde et al. |
| 2012/0107912 | A1 | 5/2012 | Hwang et al. |
| 2012/0196288 | A1 | 8/2012 | Beer |
| 2013/0078163 | A1 | 3/2013 | Chung et al. |
| 2013/0154671 | A1 | 6/2013 | Lee et al. |
| 2013/0171628 | A1 | 7/2013 | Di Carlo et al. |
| 2013/0210649 | A1 | 8/2013 | McKnight et al. |
| 2014/0011291 | A1 | 1/2014 | Patel et al. |
| 2014/0051062 | A1* | 2/2014 | Vanapalli ............ G01N 35/1002 435/2 |
| 2014/0068797 | A1 | 3/2014 | Doudna et al. |
| 2014/0076430 | A1 | 3/2014 | Miller et al. |
| 2015/0018226 | A1 | 1/2015 | Hansen et al. |
| 2016/0033378 | A1 | 2/2016 | Husain et al. |
| 2016/0123858 | A1 | 5/2016 | Kapur et al. |
| 2016/0202153 | A1 | 7/2016 | Gadini et al. |
| 2016/0223532 | A1* | 8/2016 | Rakestraw ......... C12N 15/1079 |
| 2017/0014449 | A1 | 1/2017 | Bangera et al. |
| 2017/0128940 | A1 | 5/2017 | Amini et al. |
| 2017/0145169 | A1 | 5/2017 | Oakey et al. |
| 2017/0183722 | A1 | 6/2017 | Link |
| 2018/0030515 | A1 | 2/2018 | Regev et al. |
| 2018/0078940 | A1 | 3/2018 | Lee et al. |
| 2018/0250677 | A1* | 9/2018 | Li ..................... B01L 3/502715 |
| 2018/0311669 | A1* | 11/2018 | Basu ..................... C12Q 1/025 |
| 2019/0049434 | A1* | 2/2019 | Blainey ............... G01N 33/5044 |
| 2020/0108393 | A1* | 4/2020 | Lee .................... B01L 3/502715 |

FOREIGN PATENT DOCUMENTS

| | | |
|---|---|---|
| WO | WO2015157567 A1 | 10/2015 |
| WO | WO2016040476 A1 | 3/2016 |
| WO | WO2016126871 A2 | 8/2016 |
| WO | WO2017070169 A1 | 4/2017 |

OTHER PUBLICATIONS

Inexpensive Droplet-Based Microfluidic Platform. CIDAR lab. https://www.youtube.com/watch?v=aHvfEOlh_b4.

Kamalakshakurup et al. High-efficiency single cell encapsulation and size selective capture of cells in picoliter droplets based on hydrodynamic micro-vortices. Lab Chip, 2017, 17, 4324-4333.

Brouzes, Eric, et al. "Droplet microfluidic technology for single-cell high-throughput screening." Proceedings of the National Academy of Sciences106.34 (2009): 14195-14200.

Macosko, Evan Z., et al. "Highly parallel genome-wide expression profiling of individual cells using nanoliter droplets." Cell 161.5 (2015): 1202-1214.

S. I. Rubinow and J. B. Keller, "The transverse force on a spinning sphere moving in a viscous fluid," J. Fluid Mech., vol. 11, No. 03, p. 447, Nov. 1961.

International Search Report for PCT Application No. PCT/US18155722 dated Feb. 6, 2019.

Doria, Arlene et al., "Rapid blood plasma separation with air-liquid cavity acoustic transducers", 15th International conference on miniaturized systems for chemistry and life sciences, Oct. 2-6, 2011, pp. 1882-1884.

Lee, Abraham P. et al., "Microfluidic air-liquid cavity acoustic transducers for on-chip integration of sample preparation and sample detection", Journal of laboratory automation, Dec. 2010, vol. 15, No. 6, pp. 449-454.

International Search Report Issued for PCT Application No. PCT/US2013/042735 dated Nov. 28, 2013.

International Search Report for PCT Application No. PCT/US18/56852 dated Jan. 11, 2019.

Lin, R., et al. "High efficiency cell encapsulation utilizing novel on-demand droplet generation scheme and impedance-based detection." 14th international conference on miniaturized systems for chemistry and life sciences, ed. H. Andersson-Svahn, S. Verpoorte, J. Emineus, N. Pam me. 2010.

J. Kim, M. Chung, S. Kim, D. H. Jo, J. H. Kim, and N. L. Jeon, "Engineering of a Biomimetic Pericyte-Covered 3D Microvascular Network," Plos One, vol. 10, p. e0133880, 2015.

X. Wang, D. T. T. Phan, A. Sobrino, S. C. George, C. C. W. Hughes, and A. P. Lee, "Engineering anastomosis between living capillary networks and endothelial cell-lined microfluidic channels," Lab on a Chip, vol. 16, pp. 282-290, 2016.

Mazutis, L. et al., Lab on a Chip, vol. 9, pp. 2665-2672 (2009).

Simon, M.G. et al., Label-Free Detection of DNA Amplification in Dropletsusing Electrical Impedance, 15th International Conference on Miniaturized Systems for Chemistry and Life Sciences 2011 (MicroTAS 2011), pp. 1683-1685 (Year: 2011).

Marsh et al. Room temperature ionic liquids and their mixtures—a review. Fluid Phase Equilibria 219 (2004) 93-98.

Oh, Woon Su, "Synthesis and applications of imidazolium-based ionic liquids and their polymer derivatives" (2012). Doctoral Dissertations. 1958. http://scholarsmine.mst.edu/doctoral_dissertations/1958.

Baret et. al, "Fluorescence-activated droplet sorting (FADS): efficient microfluidic cell sorting based on enzymatic activity," Lab Chip. Jul. 7, 2009; 9(13):1850-8. doi: 10.1039/b902504a. Epub Apr. 23, 2009.

International Search Report for PCT Application No. PCT/US18/36962 dated Aug. 30, 2018.

(56) References Cited

OTHER PUBLICATIONS

Murata et al., Electrochemical single-cell gene-expression assay combining dielectrophoretic manipulation with secreted alkaline phosphatase reporter system, 2009, Biosensors and Bioelectronics, 25, 913-919.
Stinson et al., Genes Expressed in the Male Gametophyte of Flowering Plants and Their Isolation, 1987, Plant Physiol., 83, 442-447.
International Search Report for PCT Application No. PCT/US2016/056683 dated Dec. 27, 2016.
International Search Report issued in PCT Application No. PCT/US18/36952, dated Sep. 18, 2018.

* cited by examiner

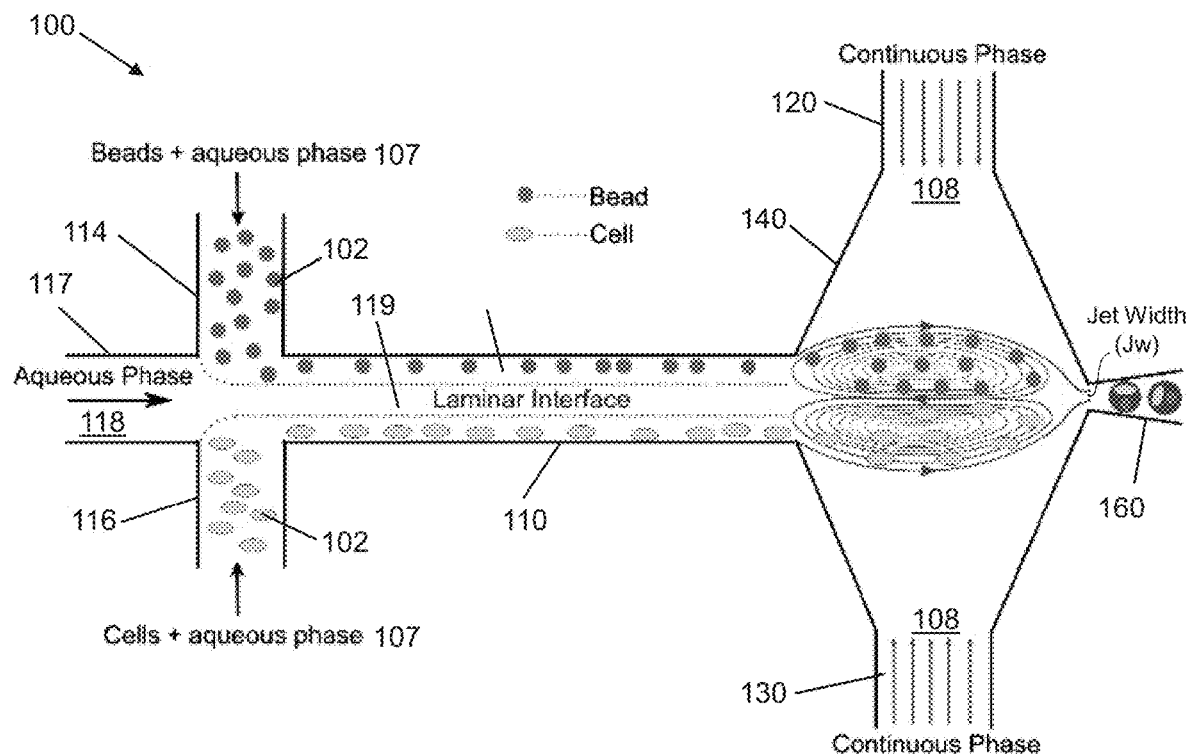
FIG. 1
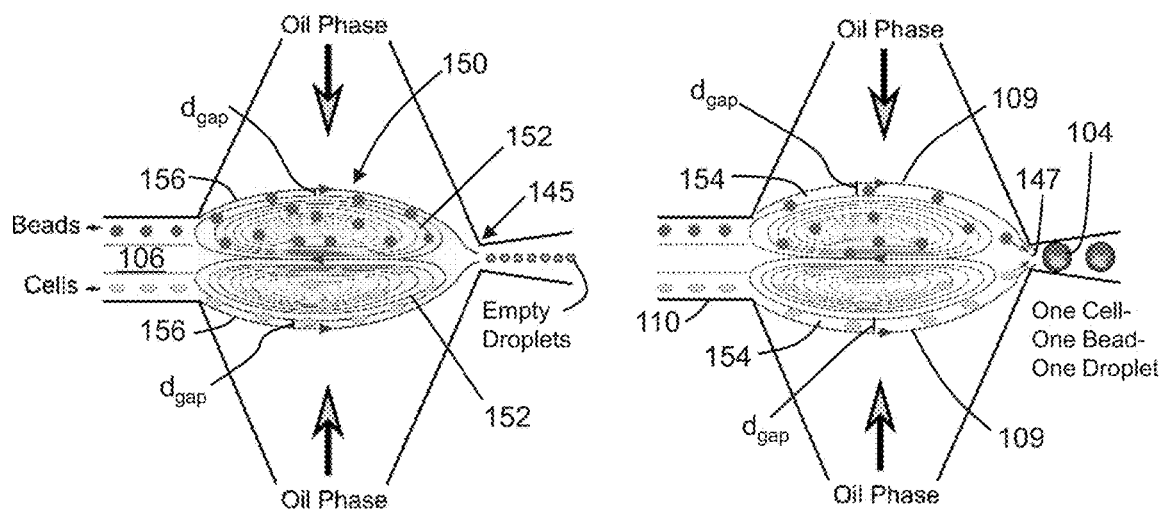
FIG. 2A
FIG. 2B

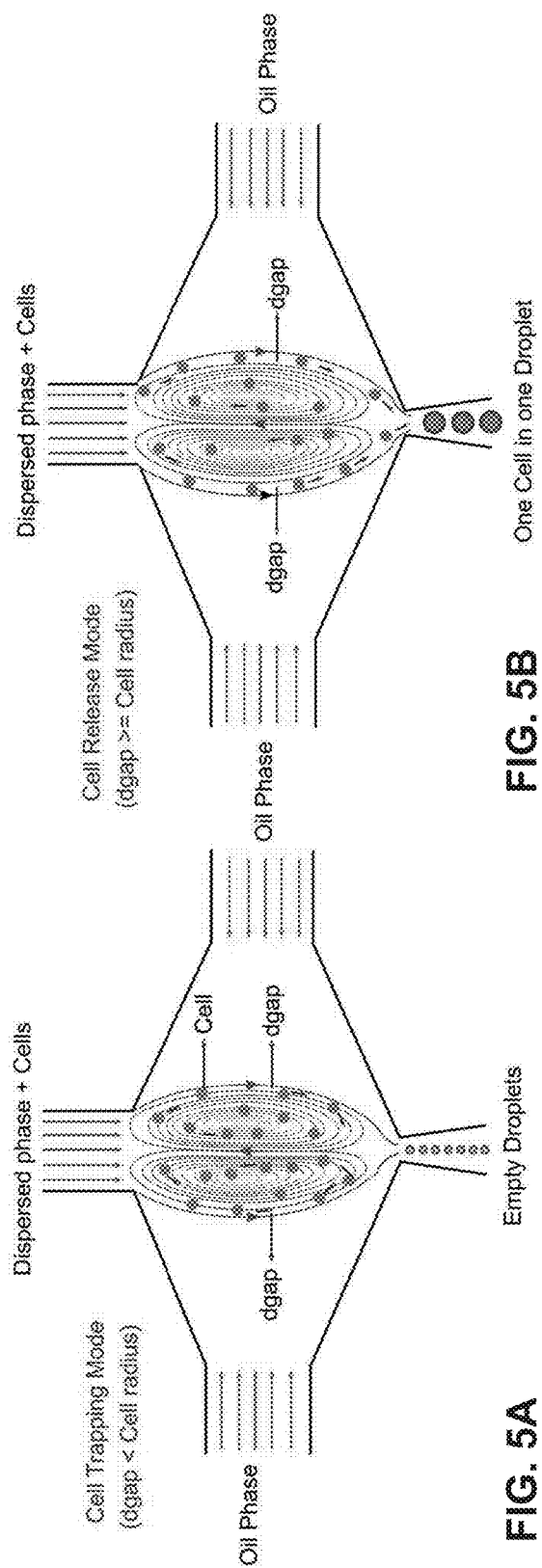
FIG. 5A
FIG. 5B
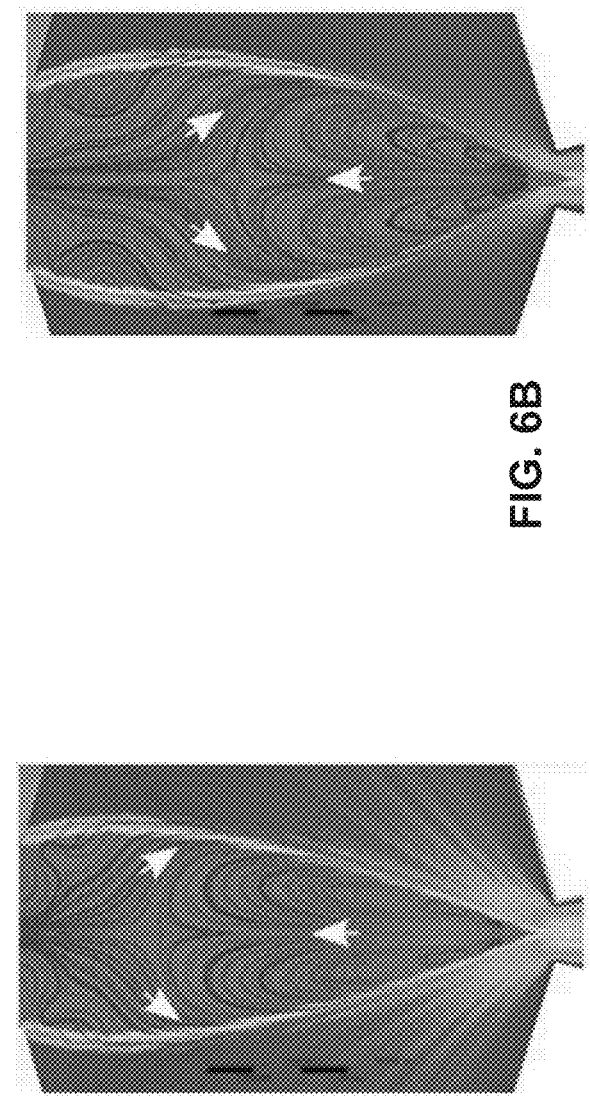
FIG. 6A
FIG. 6B

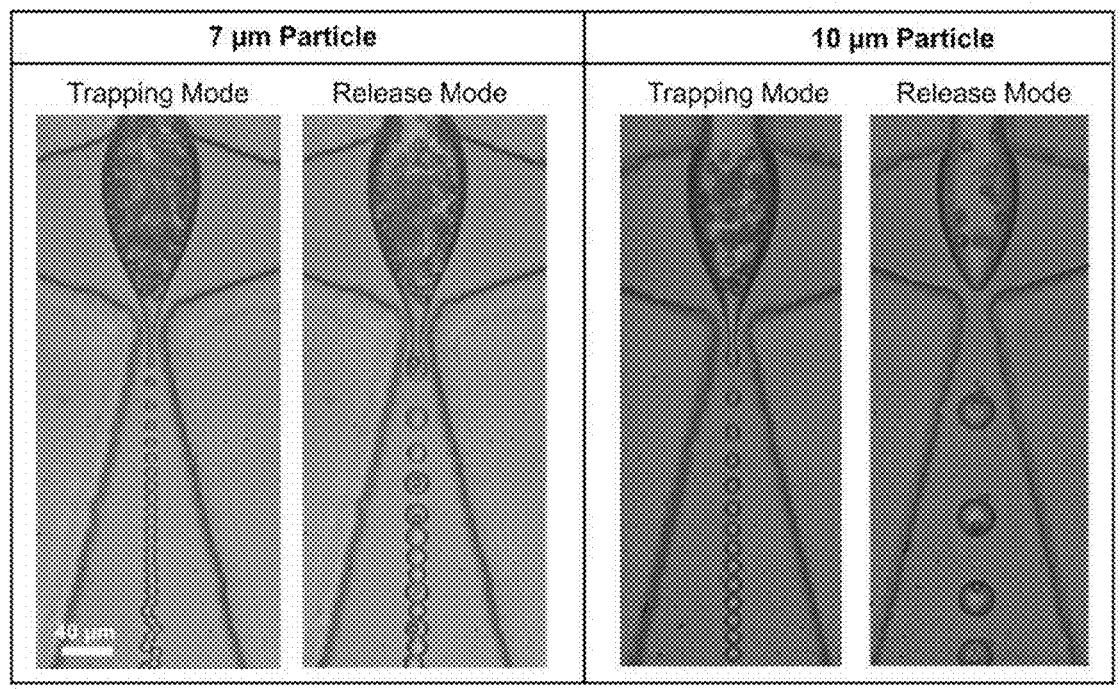
FIG. 12A                    FIG. 12B
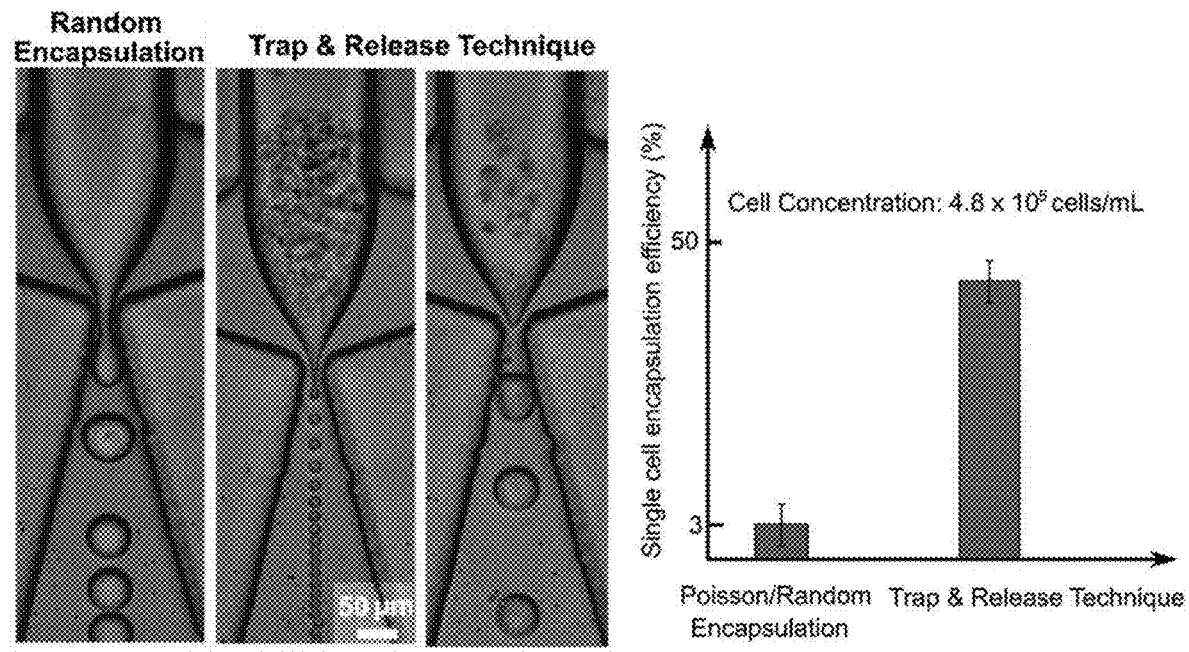
FIG. 13A    FIG. 13B    FIG. 13C

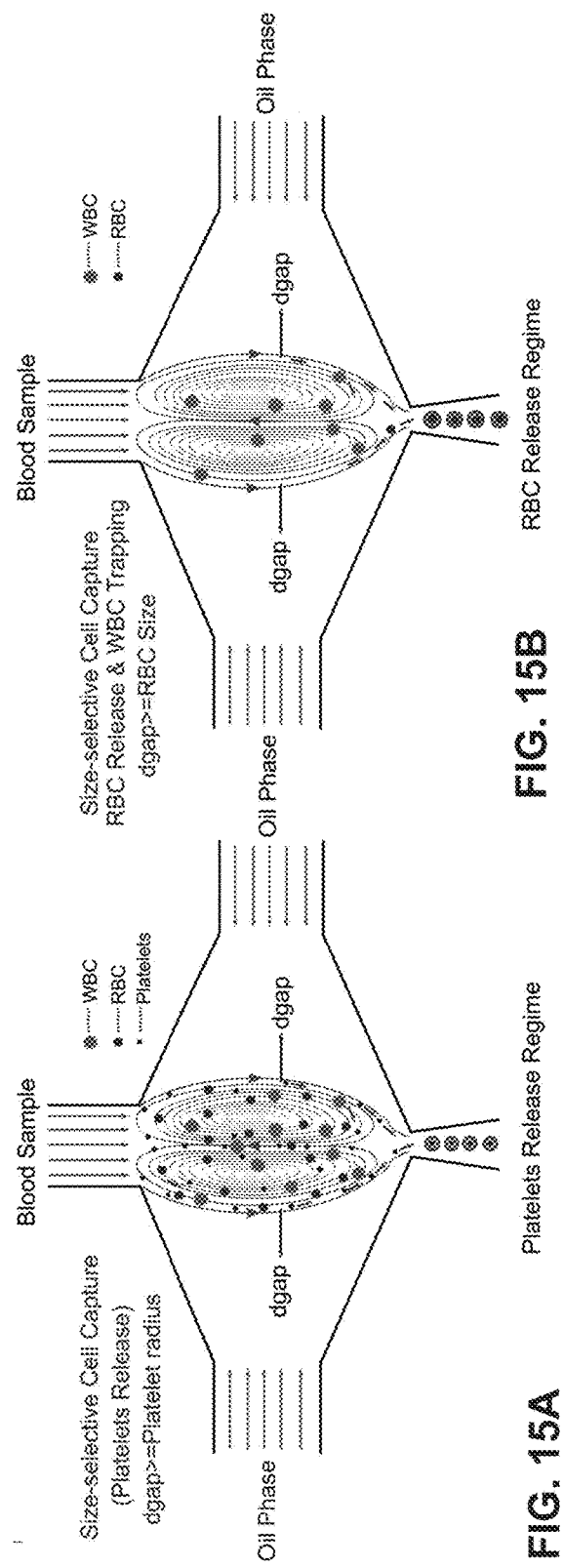
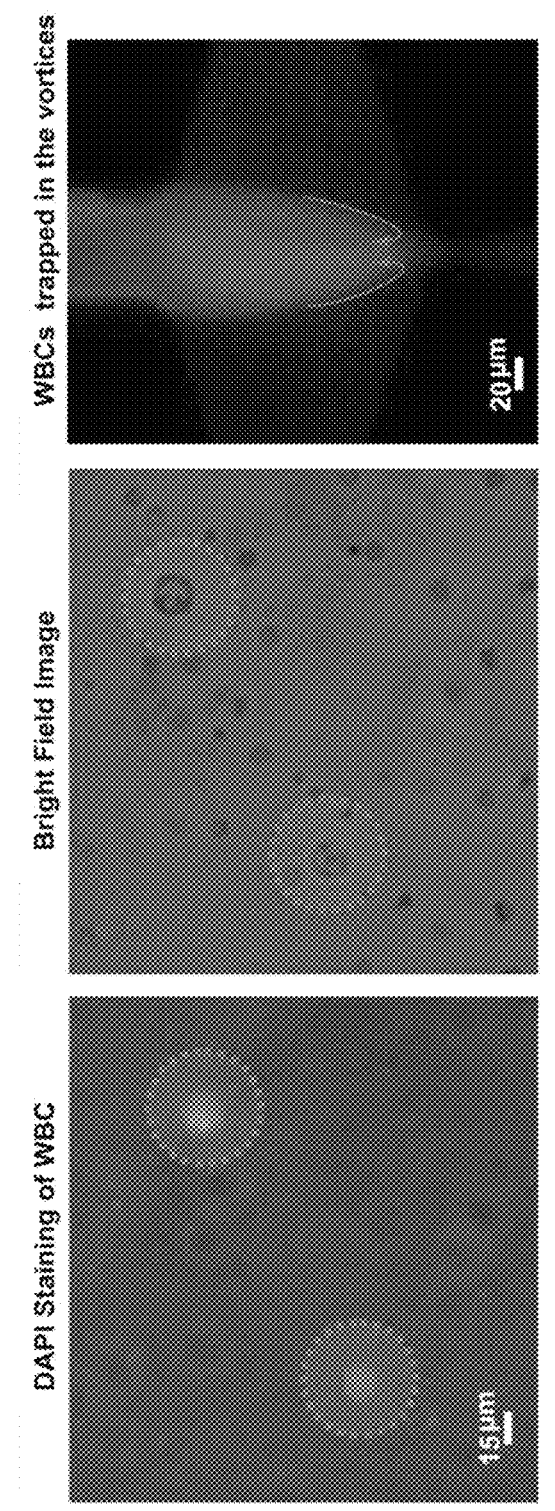
FIG. 15A
FIG. 15B
FIG. 16A
FIG. 16B
FIG. 16C

HIGH-EFFICIENCY ENCAPSULATION IN DROPLETS BASED ON HYDRODYNAMIC VORTICES CONTROL

CROSS REFERENCE

This application claims priority to U.S. Provisional Application No. 62/517,797 filed Jun. 9, 2017, the specification(s) of which is/are incorporated herein in their entirety by reference.

GOVERNMENT SUPPORT

The inventions were made with government support under Grant No. 1362165 awarded by the National Science Foundation. The government may have certain rights in the inventions.

FIELD OF THE INVENTION

The present invention relates to microfluidic devices, namely, to high-efficiency encapsulation of samples using droplet-based microfluidic devices.

BACKGROUND OF THE INVENTION

Single-cell analysis is a field that studies the genomics, transcriptomics, proteomics and metabolomics at the single cell level. Conventional techniques to perform single cell analysis are flow cytometry and automated microscopy. To address the wide range of applications for single cell analysis, these conventional methods are often coupled with microfluidic devices. Microfluidic devices and systems are configured to process (e.g., move, mix, separate) small volumes of fluid, typically in the range of picoliters to microliters. In addition, the microfluidic devices can spatially collect single cells in micro wells, patterned surfaces, and various traps based on mechanical, magnetic, hydrodynamic, optical, dielectrophoretic, and acoustic principles. These microfluidic devices can be used for various applications including printing, bio-chemical assays, drug discovery, etc. A class of microfluidic devices and systems includes microfluidic droplet generating and manipulating devices configured to manipulate discrete droplets. Droplet-based microfluidic devices can be configured to perform a variety of operations, such as, for example, transportation of droplets, storage of droplets, mixing of droplets, analysis of droplets, etc. Droplet-based microfluidic devices can be used as microreactors to achieve controlled and rapid mixing of fluids and/or to synthesize droplets and encapsulate various biological entities for biomedicine and biotechnology applications.

Droplet-based single cell assays are based on the ability to encapsulate and confine single cells in individual droplets and enable genome wide expression profiling. Most single cell encapsulations in droplets are performed randomly and dictated by Poisson statistics. However, there have been a few techniques that rely on either active or passive methods for deterministic single cell encapsulation. Active techniques involve selective single cell encapsulation in droplets using laser induced optical trapping and pico-ejection techniques; however, these methods generally operate at very low throughput (<1 Hz). Passive techniques are often dictated by the Poisson distribution, where the relative flow rates of the continuous and dispersed phases are tuned to direct the single cells into single droplets. Non-limiting examples of said passive techniques include the Rayleigh-Plateau instability jet break-up effect combined with lateral induced drift and steric interaction at the bifurcation or with deterministic lateral displacement (DLD) pillar, and inertial ordering of the cells in a curved channel or inertial focusing of the cells in a long, high aspect ratio microchannel. Both techniques have reported an encapsulation efficiency of up to 80%. However, the requirement of long microchannels for inertial spacing, high cell loading densities, and the need to control the incoming cell velocity to match the droplet generation frequency adds complexity to the system. Hence, there is a need for improved microfluidic device and method for encapsulation in single droplets.

The present invention features a novel technique that utilizes three-dimensionally confined hydrodynamic micro-vortices generated by a unique microfluidic flow focusing design that provides adequate co-shearing space for both continuous and disperse phases at a droplet generating junction. These micro-vortices function as a physical tool to trap the cells, and then released them one-to-one (1-1) into the droplets at 50% efficiency, overcoming the intrinsic limitations of Poisson statistics (<10%, if no droplets contain two or more cells in them).

SUMMARY OF THE INVENTION

It is an objective of the present invention to provide for microfluidic devices and methods for encapsulating biomolecules in droplets. Embodiments of the invention are given in the dependent claims. Embodiments of the present invention can be freely combined with each other if they are not mutually exclusive.

In some aspects, the present invention provides a hydrodynamic technique that can accomplish two critical operations: (i) high-efficiency single cell encapsulation and (ii) size-selective sorting of cells. The hydrodynamic technique comprises an initial trapping of cells in micro-vortices and later release of said cells one-to-one into droplets, said steps being controlled by a width, $d_{gap}$, of the outermost streamlines adjacent to a liquid-liquid interface. For example, if the radius of the cell is greater than $d_{gap}$, the cells will not enter the droplets, and instead will recirculate within the vortex. If the radius of the cell is comparable to the $d_{gap}$, the cells will enter the droplets one-by-one while recirculating in the vortex. Moreover, $d_{gap}$ can be further adjusted to perform size-selective sorting of cells. Size-selective sorting is realized by trapping different size cells in the vortices and releasing them into the droplets in the order of their sizes by modulating the $d_{gap}$. To the inventors' knowledge, this is the first technique that could perform both single cell encapsulation and size selective cell sorting in a single microfluidic device. None of the presently known prior references or work has this unique inventive technical feature of the present invention.

As will be described herein, by changing the dispersed to continuous phase pressure ratio ($\varphi$), $d_{gap}$ can be precisely tuned to enable trapping and release modes, thereby achieving maximum encapsulation efficiency. One of the significant advantages of this unique trap and release mechanism is that it can perform high efficiency single cell encapsulations at low cell loading densities. This is due to the cells being initially trapped in the micro-vortices, thereby increasing the cell concentration locally before encapsulation. Compared to Poisson statistics, the present invention was able to achieve greater than 10× single cell encapsulation efficiency, as compared to current encapsulation techniques, using the same cell concentration in a bulk solution. In addition, the present invention will be further described to perform size-selective sorting of samples, which is an important sample processing step in liquid biopsy. For example, the trap and release mechanism was able to separate of white blood cells (WBCs) from 10×PBS diluted blood sample at 60-80% capture efficiency. Small cells including the platelets (2-3 μm) and red blood cells (RBCs) (6-7 μm) were released from the vortices and encapsulated into droplets by tuning $d_{gap}$ to be approximately in their size range.

In other aspects, the innovative technique of this invention can be implemented in a microfluidic device that includes a microfluidic channel configured to transport a dispersed phase comprising solid samples dispersed in a first liquid, a microfluidic channel configured to transport a continuous phase comprising a second liquid immiscible with the first liquid, said microfluidic channels configured to intersect in an intersection region, and an output microfluidic channel in fluid communication with the intersection region through an orifice. The first microfluidic channel can be configured to receive the dispersed phase from a plurality of incoming microfluidic channels. The present invention aims to improve cell/bead encapsulation efficiency using flow parameter modulation, such as with a fluid controller that is configured to vary flow velocity and/or fluid pressure. The fluid controller can be configured to switch the microfluidic device between the trapping mode and a release/encapsulation mode. In the trapping mode, the fluid controller is configured to adjust the flow rates and/or fluid pressures of the continuous phase and/or the dispersed phase to generate vortices in the intersection region that trap the solid samples in the dispersed phase, thereby increasing the concentration of the solid samples before encapsulation to provide high efficiency and throughput. In the release/encapsulation mode, the fluid controller is configured to adjust the flow rates of the continuous phase and/or the dispersed phase to form droplets encapsulating the samples.

In various embodiments of the microfluidic device, the fluid controller can be configured to adjust flow rates and/or fluid pressures of the continuous phase and the dispersed phase such that a distance ($d_{gap}$) between an outermost streamline of the vortex and a high shear interface between the dispersed phase and the continuous phase is greater than or equal to a size of the plurality of particles. The value of the $d_{gap}$ can be varied by adjusting the flow rates and/or fluid pressures of the continuous phase and the dispersed phase so that particles of different sizes can be trapped in the vortices. Accordingly, the microfluidic device discussed herein can be used to sort particles of different sizes. In various embodiments, the continuous phase fluid can comprise a lipid and/or the dispersed phase can comprise an aqueous material. In various embodiments, the plurality of particles can comprise biological cells or particles. The size of the samples can be in the range of about 2.5-20 microns.

A surprising result of the present invention is the vortex generation in dripping and jetting regimes. Precise control over critical parameters, such as the flow rates of the fluids, generated vortices that were independent of each other so that different samples could be entrapped in their own vortex, which allowed for one sample-one sample-one droplet (1-1-1) encapsulation. This technique can be used in a variety of applications including, but not limited to, single cell encapsulation, size-selective cell trapping and release, 1 cell-1 bead encapsulation, 1 cell-1 cell encapsulation, and vortex mixing. For instance, the present invention can advantageously expand the capabilities of droplet microfluidics for performing high throughput single cell assays in a wide range of 'omics' sciences and applications.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE DRAWINGS

The features and advantages of the present invention will become apparent from a consideration of the following detailed description presented in connection with the accompanying drawings in which:

FIG. 1 shows an exemplary mechanism of trapping cells and beads in an upper and lower vortex, respectively, followed by one-one-one (1-1-1) encapsulation, according to an embodiment of the present invention. Beyond a capillary number threshold, a relative shear imposed by a continuous phase on a dispersed phase results in three-dimensionally confined two independent vortices at the junction. Beads introduced from upper inlet are trapped in the upper vortex while cells flowed in through the lower inlets are trapped in the lower vortex.

FIGS. 2A-2B show schematics of trapping mode and release mode respectively, herein collectively referred to as vortex mode. In FIG. 2A, the beads and the cells introduced from upper and lower inlets are initially trapped in the independent vortices. Intermixing of beads and cells are minimized by controlling the relative flow rates of the continuous and aqueous phases. In FIG. 2B, the beads and the cells are later released by precisely controlling flow rate ratio/droplet size.

FIGS. 5A-5B show non-limiting examples of single cell encapsulation schematics. In the cell trapping mode of FIG. 5A, when $d_{gap}$ is smaller than the radius of the cells, all the cells get trapped and recirculate within the micro-vortices. In the cell release mode of FIG. 5B, increasing $d_{gap}$ to be comparable to the radius of the cell enables one-to-one encapsulations FIG. 6A shows a non-limiting computational fluid dynamic model (CFD) of the cell trapping mode.

FIG. 6B shows a non-limiting CFD model of the cell release mode.

FIG. 8A show a trapping of 2.5 μm beads in the micro-vortex. In FIG. 8B, jet breaking in the presence of beads leads to smaller droplets with beads in them. Empty droplets are larger in diameter compared to the bead-containing droplets. In FIG. 8C, the presence of the bead breaks the jet.

FIGS. 12A-12B shows vortex mode encapsulation of 7.32 μm and 10 μm beads ($\varphi$=0.19 for trapping and 0.23 for release) in the dripping regime.

FIGS. 13A-13B is a comparison of the trap and release mechanism with random encapsulation at a fixed concentration. Unlike the random encapsulation, trapping increases the local concentration of cells in the micro-vortex before encapsulation, which increases the efficiency by greater than 10 times.

FIG. 13C is an efficiency comparison chart of the trap and release technique versus random encapsulation.

FIGS. 15A-15B show single cell encapsulation schematics of size selective capture and release of platelets, RBCs and WBCs from the blood sample. FIG. 15A is an example schematic of a blood platelet release regime. The $d_{gap}$ is tuned to be comparable to the radius of the platelets as RBCs and WBCs are trapped and recirculate within the micro-vortices. FIG. 15B is an example schematic of a blood RBC release regime. Trapped blood cells are released in ascending order of their sizes by gradually increasing $d_{gap}$ such that following the platelets, RBCs and then WBCs are released. This technique utilizes the micro-vortex as a tool to perform size-selective capture of the cells from the sample.

FIGS. 16A-16C show DAPI stained WBCs, bright field image of the same, and visualization of WBCs trapped in the recirculation vortices, respectively.

DESCRIPTION OF PREFERRED EMBODIMENTS

Figure 3A:
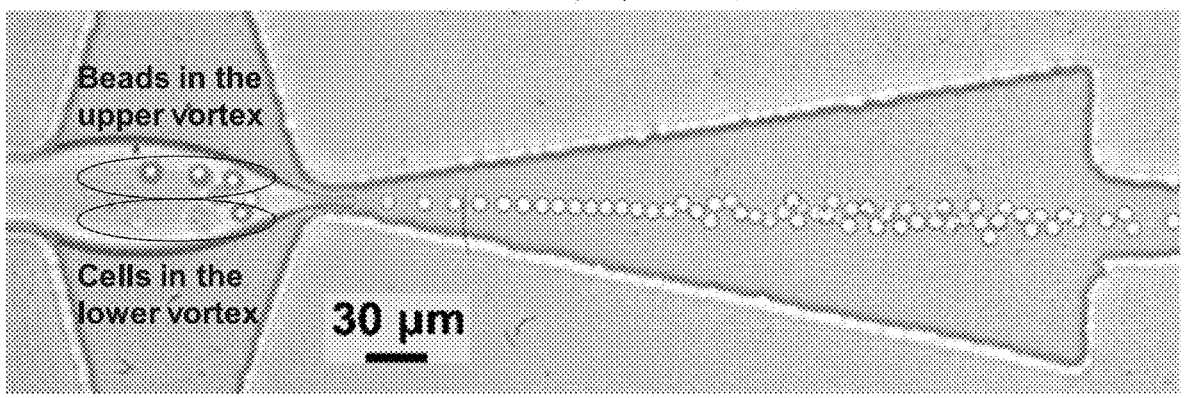
FIG. 3A shows a trapping of 10 μm beads in the upper vortex and K-562 cells in the lower vortex.
Figure 3B:
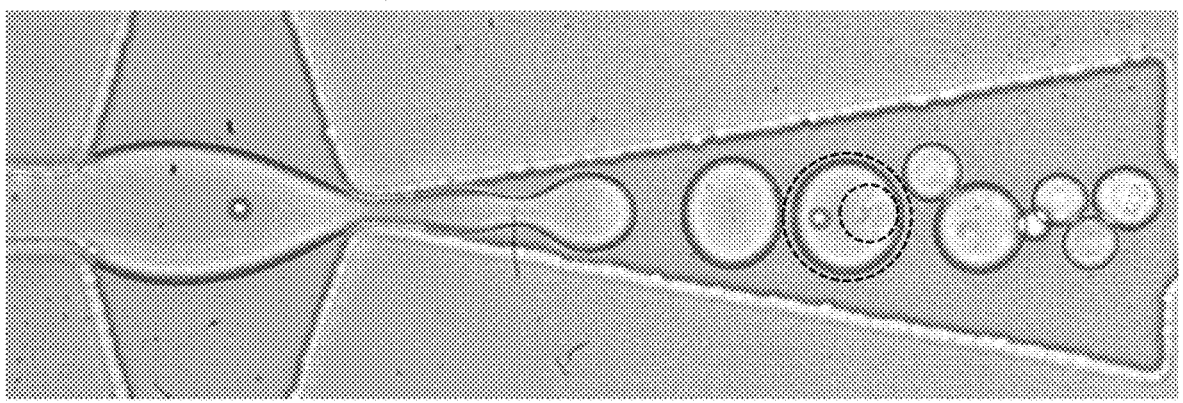
FIG. 3B shows a release of 10 μm beads and k-562 cells into the droplets. The dashed circle shows a 1-1-1 droplet, and the dashed circle within the droplet indicates a presence of a cell.
Figure 4:
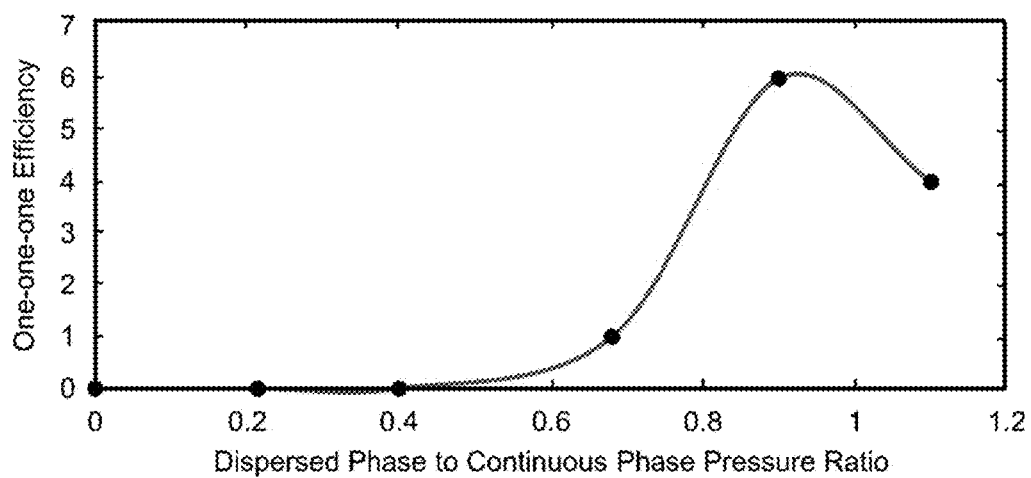
FIG. 4 is a graph of 1-1-1 encapsulation efficiency vs. pressure ratio of dispersed phase to continuous phase ($\varphi$) using vortex mode with low cell concentrations.
Figure 7A:
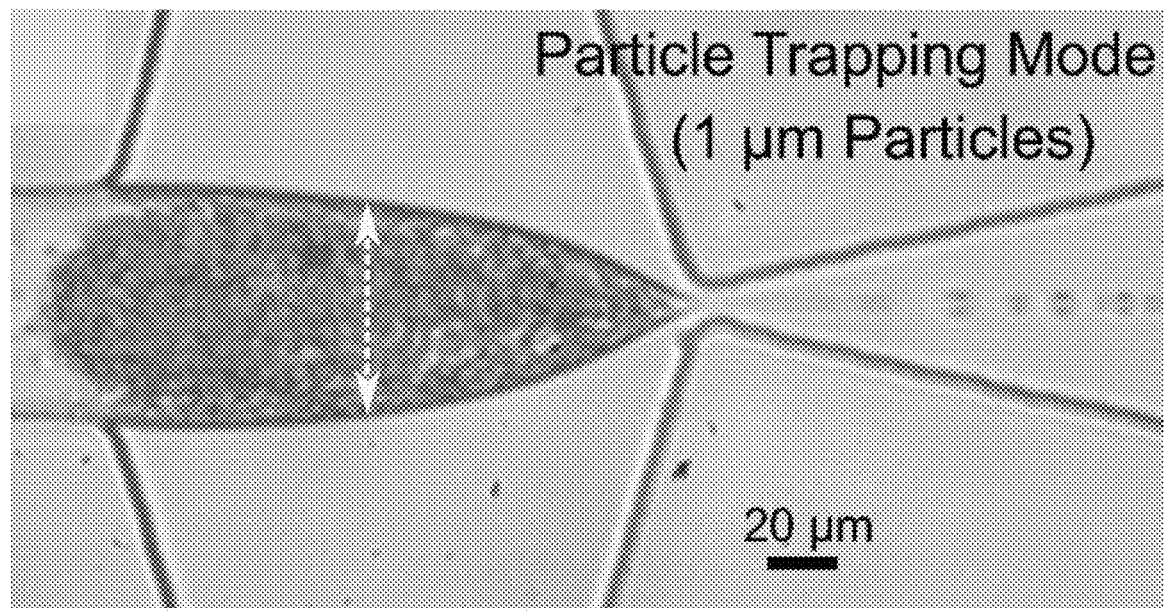
FIGS. 7A-7B show exemplary images of 1 μm single particle encapsulation using vortex mode.
Figure 7B:
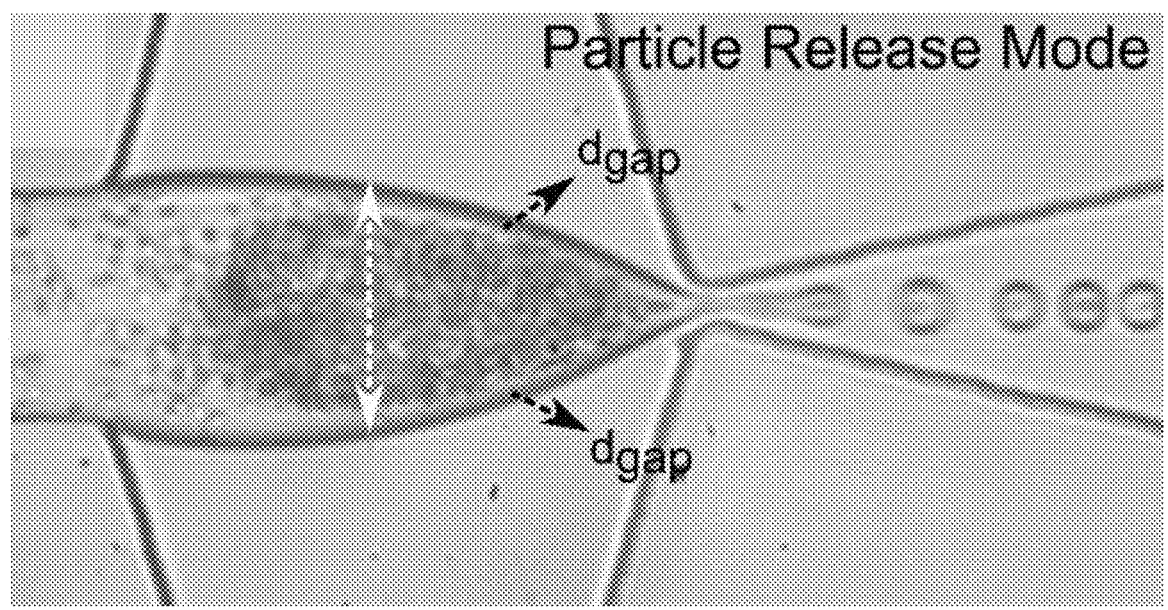
Figures 8A, 8B, 8C:
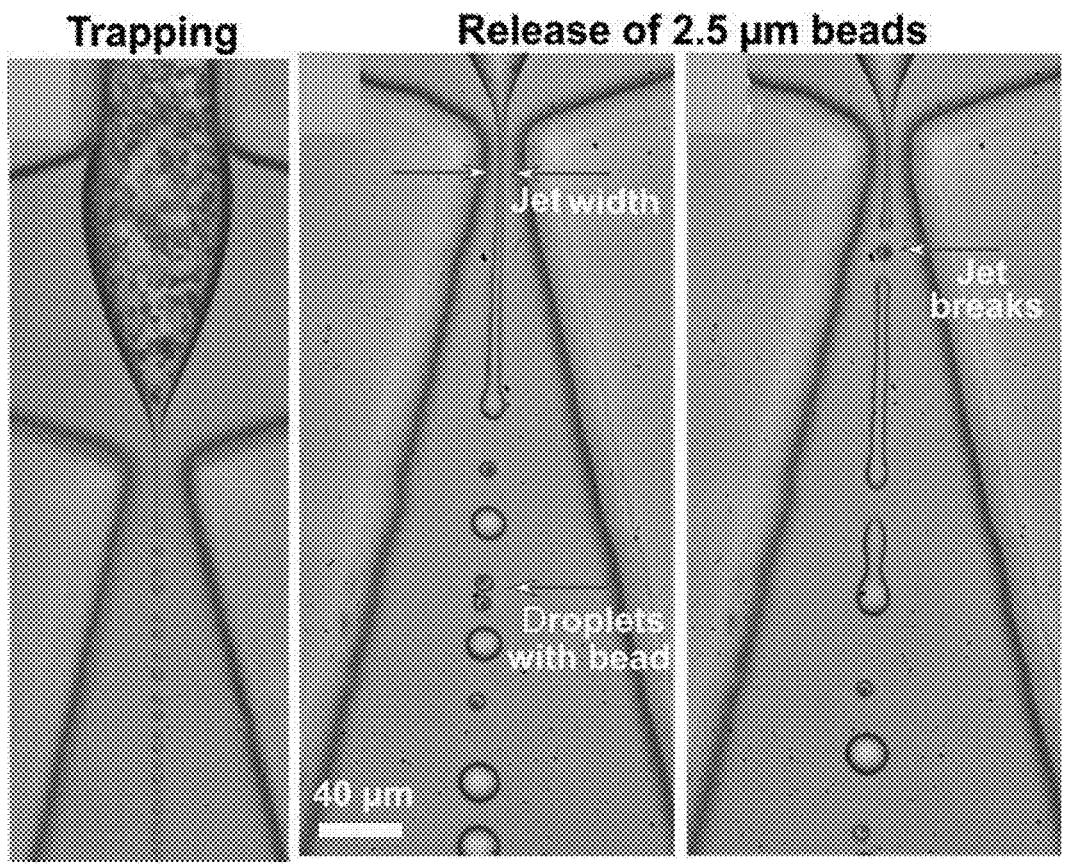
FIGS. 8A-8C show a vortex mode encapsulation of beads in the jetting regime.

Following lists elements corresponding to a particular element referred to herein:
100 microfluidic device
102 solid sample
104 droplet
106 dispersed phase fluid
107 flow stream
108 continuous phase fluid
109 high shear interface
110 combining channel
114 first dispersed phase channel
116 second dispersed phase channel
117 aqueous phase channel
118 aqueous phase fluid
119 laminar interface stream
120 first continuous phase channel
130 second continuous phase channel
140 intersection region
145 droplet shearing junction
147 orifice
150 vortex region
152 vortex
154 outer stream
156 outermost streamline
160 output channel
170 fluid flow controller As used herein, the microfluidic devices employ fluid volumes on the scale of microliters ($10^{-6}$) to picoliters ($10^{-12}$) that are contained within sub-millimeter scale channels. The structural or functional features may be dimensioned on the order of mm-scale or less, preferably in the micron scale or less. For example, a diameter or width of a channel or a dimension of an intersection or junction may range from <0.1 μm to greater than 1000 μm. Alternatively or in addition, a length of a channel may range from 0.1 μm to greater than cm-scale. The microfluidic device may employ active or passive techniques for fluid transport and droplet production. Compared to the active approach, in which fluid manipulation involves the use of micropumps and microvalves, the passive approach takes advantage of the characteristic flow field in microfluidics to control the interface and capillary instability, and consequently produce droplets.

As used herein, the term "high shear interface" refers to a high velocity liquid-liquid interface formed between two immiscible liquids. Generally, the continuous phase flow rate is greater than the flow rate of the dispersed phase. For instance, the continuous phase flow rate may be about 2-5 times greater. At the aqueous-oil interface, the high continuous phase flow rate imparts the same velocity to the dispersed phase at the interface. Hence, the dispersed phase at the interface is at a higher velocity (shear) than the bulk. As used herein, the term "laminar flow" refers to flow of a fluid in layers that do not mix. One of ordinary skill in that art would understand that at lower Reynold's numbers (<10), a laminar flow is always established in the microfluidic channel. The fluid flows in parallel layers with no lateral mixing but with some minor diffusion.

Samples for Encapsulation

In various embodiments of the present invention, the samples for encapsulation may be microparticles. In some embodiments, the microparticles may be beads. Examples of beads include, but are not limited to, polymer beads, barcoded beads, functionalized beads, and magnetic beads. In some embodiments, the beads may have a size or dimension, such as a diameter or width, ranging from about 0.01 µm to about 20 µm.

In other various embodiments of the present invention, the samples for encapsulation may be cells. Any particular cell type from any organism may be used in the methods and systems of the present invention. The cells may have a size or dimension, such as a diameter or width, ranging from about 0.1 µm to about 20 µm. In some embodiments, the cells may be wild type cells or genetically modified cells. In other embodiments, the cells may be cells harboring one or more mutations, healthy cells, diseased cells or unhealthy cells, etc. For example, in some embodiments, the cells may be prokaryotic cells (e.g., bacteria, archaebacteria, etc.). In other embodiments, the cells may be eukaryotic cells such as single-celled eukaryotes, fungal cells (e.g. yeast, mold, etc.), animal cells, mammalian cells (e.g. cells from a human, non-human primate, rodent, rabbit, sheep, dog, cat, etc), and non-mammalian cells (e.g. cells from insects, reptiles, amphibians, birds, etc.).

In some embodiments, the cells used in the present invention may be other eukaryotic cells such as plant cells or algal cells. Non-limiting and non-exhaustive examples of plant cells include cells from corn, soybean, wheat, cotton, grass, flowering plants, fruit-bearing plants, trees, tuberous plants, potatoes, root plants, carrots, peanut, nuts, beans, legumes, and squashes. It is to be understood that the term "plant cell" encompasses all types and stages of plant cells and is not limited to the aforementioned examples. Non-limiting and non-exhaustive examples of algal cells include cells from *Chlorella* sp., *Nannochloropsis* sp, and *Botryococcus* sp. It is to be understood that the term "algal cell" encompasses all types of algal cells and is not limited to the aforementioned examples. One of the distinguishing characteristics that plant and algal cells have over animal cells is a cell wall that surrounds a cell membrane to provide rigidity, strength, and structure to the cell. The cell wall may be comprised of polysaccharides including cellulose, hemicellulose, and pectin. Similar to plant and algal cells, the fungal cells also have a cell wall, which may be comprised of polysaccharides including glucans, mannans, and chitin.

In other embodiments, the cells used in the present invention may be protoplasts, which are intact plant, bacterial or fungal cells that had its cell wall completely or partially removed using either mechanical or enzymatic means.

In yet other embodiments, the cells used in the present invention may be a tetrad. The term "tetrad" is used to herein to refer to a single structure comprised of four individual physically attached components. A "microspore" is an individual haploid structure produced from diploid sporogenous cells (e.g., microsporoyte, pollen mother cell, or meiocyte) following meiosis. A microspore tetrad refers to four individual physically attached microspores. A "pollen grain" is a mature gametophyte containing vegetative (non-reproductive) cells and a generative (reproductive) cell. A pollen tetrad refers to four individual physically attached pollen grains.

Encapsulation

Referring now to FIG. 1, in some embodiments, the present invention features a microfluidic device (100) for encapsulating a sample (102) in a droplet (104). The microfluidic device (100) may comprise a combining channel (110) having a dispersed phase fluid (106) flowing therein at a first flow rate ($v_d$), and a continuous phase channel network (120) having a continuous phase fluid (108) flowing therein at a second flow rate ($v_c$). In one embodiment, the dispersed phase fluid (106) may comprise at least two flow streams (107) with one or both of said flow streams (107) comprising dispersed samples (102). In some embodiments, the continuous phase channel network (120) can have two portions that are each disposed on opposite sides of the combining channel (110) and that intersect the combining channel (110) orthogonally.

In further embodiments, the device includes an intersection region (140) formed by the continuous phase channel network (120) intersecting a terminal end of the combining channel. The continuous phase fluid (108) can intersects the dispersed phase fluid (106) to form a high shear interface (109) with the dispersed phase fluid. In some embodiments, the intersection region may comprise a droplet shearing junction (145) formed as the continuous phase fluid (108) merges with the dispersed phase fluid (106), and a vortex region (150) comprising two vortices each formed by one of the flow streams (107). The droplet shearing junction (145) may comprise an orifice (147) that fluidly couples an output channel (150) to the intersection region (140).

In other embodiments, the device further comprises a fluid flow controller (170) configured to perform operations comprising adjusting $v_d$, $v_c$, or both to trap and re-circulate the samples (102) within the vortices (152), and adjusting $v_d$, $v_c$, or both to release the samples (102) from the vortices (152) and generate droplets (104) encapsulating at least one sample (102) at the droplet shearing junction (145). In one embodiment, the fluid flow controller (170) may comprise a feedback control system. The feedback control system may be configured to actuate a pressure controller to adjust the pressure to release the cells/particles if the intensity of the flow focusing junction exceeds a certain threshold. In some embodiments, intensity can be measured using an image processing module. In other embodiments, the pressure controller can be regulated using LabView program.

The microfluidic devices described herein may be used to create droplets of a fluid (e.g., oil or water) for chemical reactions, assays, in drug delivery, in drug discovery, etc. In some embodiments, the present invention features a method for encapsulating a sample (102) in a droplet (104). The method may comprise providing a microfluidic device (100) comprising a combining channel (110), a first continuous phase channel (120) having a portion thereof disposed on one side of the combining channel, a second continuous phase channel (130) having a portion thereof disposed on an opposite side of the combining channel such that said portions of the first and second continuous phase channels intersect at a terminal end of the combining channel to form an intersection region (140), and an output channel (160) fluidly coupled to the intersection region (140). A dispersed phase fluid (106) flows through the combining channel (110) at a first flow rate ($v_d$). In some embodiments, the dispersed phase fluid (106) may at least two flow streams (107) with one or both of said flow streams (107) containing dispersed samples (102). A continuous phase fluid (108) is co-flowing through each of the first and second continuous phase channels (120, 130) at a second flow rate ($v_c$). In some embodiments, the continuous phase fluid (108) intersects the dispersed phase fluid (106) at the intersection region (140) such that a droplet shearing junction (145) is formed within the intersection region (140) as the continuous phase fluid (108) merges with the dispersed phase fluid (106). The droplet shearing junction (145) can comprise an orifice (147) fluidly coupling the output channel (160) to the intersection region (140).

In some embodiments, the method may further comprise adjusting $v_d$, $v_c$, or both such that the continuous phase fluid (108) forms a high shear interface (109) with the dispersed phase fluid (106) at the intersection region (140), adjusting $v_d$, $v_c$, or both to generate a vortex region (150) in the dispersed phase fluid (106) at the intersection region (140), where the vortex region (150) comprises two vortices (152) each formed by one of the flow streams (107), adjusting $v_d$, $v_c$, or both to trap and re-circulate the samples (102) within the vortices (152), and adjusting $v_d$, $v_c$, or both to release the samples (102) from the vortices (152) and generate droplets (104) encapsulating one sample (102) at the droplet shearing junction (145).

Without wishing to limit the present invention to a particular theory or mechanism, the occurrence of the microvortices (152) in the aqueous/dispersed phase may depend on the combined effects of the aqueous-oil (dispersed phase-continuous phase) interfacial shearing rate ($\alpha$) and the tip oscillation frequency (TOF), defined as the interfacial oscillation frequency of the droplet generation tip. As used herein, an approximate range of $\alpha$ is about 1-200 [1/s], with $\alpha$ increasing as the regime changes from squeezing to dripping to jetting. In some embodiments, the range of $\alpha$ in the squeezing regime may be about 1-50 $s^{-1}$, the range of $\alpha$ in the dripping regime may be about 50-100 $s^{-1}$, and the range of $\alpha$ in the jetting regime may be about 100-200 $s^{-1}$. The protrusion and retraction of the droplet generation tip occurs each time a droplet is generated; therefore, the tip oscillation frequency (TOF) is equal to the number of droplets generated per second($f$).

Both the parameters $\alpha$ and TOF can vary with droplet generation regimes such that they are lowest in the squeezing regime and highest in the jetting regime, which is dictated by the capillary number ($Ca=\mu V_c/\sigma$), where $\mu$ is the viscosity of the continuous phase, $V_c$ is the velocity of the continuous phase and $\sigma$ is the interfacial tension between the phases. Again, without wishing to limit the present invention, the microvortices may start to occur at higher values of $\alpha$ and TOF. In the squeezing regime, which occurs at lower Ca (e.g., about $10^{-3}$), both the interfacial shearing rate ($\alpha$) and the TOF, which may be about 50 Hz, are not large enough to generate the microvortices. However, at a higher Ca (e.g., about $10^{-1}$) where the regime switches from squeezing to dripping, the microvortices are likely to occur because of the increase in $\alpha$ and TOF, for instance, the TOF may be greater than >2000 Hz.

Referring to FIG. 2A-2B, each vortex (152) can have an outer stream (154) disposed between an outermost streamline (156) of the vortex and the adjacent high shear interface (109). Each outer stream (154) may be fluidly coupled to the orifice (147) so as to be outputted into the output channel. The outer streams (154) can have a maximum width, $d_{gap}$, between the outermost streamline (156) of each vortex and the adjacent high shear interface (109). In one embodiment, $d_{gap}$ can be reduced when adjusting the flow rates to trap and re-circulate the samples (102). In another embodiment, $d_{gap}$ can be widened when adjusting the flow rates to release the samples (102) from the vortices (152) and into their respective outer stream (154) for encapsulation at the droplet shearing junction (145).

Without wishing to limit the present invention to a particular theory or mechanism, $v_d$, $v_c$, or both can be adjusted such that a ratio of $v_d$ to $v_c$ reduces $d_{gap}$ to be less than half a diameter of the samples, thereby trapping, re-circulating, and accumulating the samples (102) within the vortices (152), and further reducing a width of the orifice to prevent encapsulation. In another embodiment, $v_d$, $v_c$, or both can be adjusted such that the ratio of $v_d$ to $v_c$ increases $d_{gap}$ to be about ½-1.5 the diameter of the samples, thereby releasing the samples from the vortices into the outer streams, and further increasing the width of the orifice to allow for encapsulation of a single sample in one droplet, or co-encapsulation of two different samples in one droplet.

In one embodiment, as shown in FIGS. 1-3B, the dispersed samples (102) may comprise a plurality of cells flowing in one flow stream (107), and a plurality of particles flowing in the other flow stream (107). When the cells and particles flow into the intersection region (140), the cells may be disposed in one vortex (152a) and the particles may be disposed in the other vortex (152b). In a preferred embodiment, when adjusting the flow rate for release, one cell is released from its vortex (152a) into its outermost stream (154a) and one particle is released from its vortex (152b) into its outermost stream (154b). The one cell and the one particle are then co-encapsulated in the one droplet (104) as said droplet is formed at the droplet shearing junction (140), and the droplet (104) co-encapsulating the one cell and one particle is released from the orifice (147) into the output channel (160).

Referring to FIGS. 5A-14, in an alternative embodiment, the dispersed samples (102) may either be cells or particles. One sample, e.g. one cell or one particle, may be encapsulated as the droplet (104) is formed at the droplet shearing junction (140). The droplet (104) encapsulating the one sample (102) is then released from the orifice (147) into the output channel (160).

According to an exemplary embodiment, the method for encapsulating the solid sample (104) in a droplet (102) may comprise flowing a first fluid (106) through a first microfluidic channel (110) at a first flow rate ($v_d$), and co-flowing a second fluid (108) through each of a second microfluidic channel (120) and a third microfluidic channel (130) at a second flow rate ($v_c$). The second and third microfluidic channels (120, 130) may intersect the first microfluidic channel (110) to form an intersection region (140) such that the second fluid streams (108) intersect the first fluid (106) and merge to form a droplet shearing junction (145) within the intersection region (140). In one embodiment, the first fluid (106) may comprise at least two flow streams (107) with one or both of said flow streams (107) comprising dispersed solid samples (102). The method further comprises adjusting $v_d$, $v_c$, or both to generate a vortex region (150), which comprises two vortices (152) each formed by the flow streams (107), in the first fluid (106) at the intersection region (140), adjusting $v_d$, $v_c$, or both to trap and re-circulate the samples (102) within the vortices (152), adjusting $v_d$, $v_c$, or both to release the samples (102) from the vortices (152), and generating droplets (104) at the droplet shearing junction (145) that encapsulate one solid sample or co-encapsulate two different solid samples. Without wishing to limit the present invention, the first liquid flowing through the first channel (e.g., water) is broken up to form discrete droplets as a result of shear forces from the second liquid. The size of the first liquid droplets can depend on a variety of factors including, for examples, the flow rate of the second liquid. For example, as the flow rate of the second liquid is increased, the size of the first liquid droplets is reduced.

According to another embodiment, the present invention also features a method for size-selective sorting and encapsulation of a solid sample (102) in a droplet (104). This method may be implemented using any one of the microfluidic devices described herein. For instance, in one embodiment, the method may comprise providing the microfluidic device (100) comprising a combining channel (110), a first continuous phase channel (120) having a portion thereof disposed on one side of the combining channel, a second continuous phase channel (130) having a portion thereof disposed on an opposite side of the combining channel such that said portions of the first and second continuous phase channels intersect at a terminal end of the combining channel to form an intersection region (140), and an output channel (160) fluidly coupled to the intersection region (140). The method also comprises flowing a dispersed phase fluid (106) through the combining channel (110) at a first flow rate ($v_d$), and co-flowing a continuous phase fluid (108) through each of the first and second continuous phase channels (120, 130) at a second flow rate ($v_c$). In some embodiments, the dispersed phase fluid (106) may comprise at least two flow streams (107), with one or both of said flow streams (107) comprising dispersed samples (102) having varying sizes. In some preferred embodiments, the continuous phase fluid (108) may intersect the dispersed phase fluid (106) at the intersection region (140) such that a droplet shearing junction (145) is formed as the continuous phase fluid (108) merges with the dispersed phase fluid (106). The droplet shearing junction (145) may comprise an orifice (147) fluidly coupling the output channel (160) to the intersection region (140).

Moreover, the method may further include adjusting $v_d$, $v_c$, or both such that the continuous phase fluid (108) forms a high shear interface (109) with the dispersed phase fluid (106) at the intersection region (140), adjusting $v_d$, $v_c$, or both to generate a vortex region (150), comprising two vortices (152) each formed by one of the flow streams (107), in the dispersed phase fluid (106) at the intersection region (140), adjusting $v_d$, $v_c$, or both to trap and re-circulate the samples (102) within the vortices (152), and adjusting $v_d$, $v_c$, or both to release samples (102) of smallest size from the vortices (152) and generate droplets (104) encapsulating one of said samples (102) at the droplet shearing junction (145), all the while the larger-sized samples (102) remain trapped in the vortices (152). The step of adjusting $v_d$, $v_c$, or both may be repeated such that release of similarly-sized samples from the vortices (152) and droplet encapsulation of one such solid sample occur in groupings ordered from smaller-sized samples to largest-sized solid samples.

Consistent with previous embodiments, each vortex (152) can have an outer stream (154) disposed between an outermost streamline (156) of the vortex and the adjacent high shear interface (109). Each outer stream (154) may be fluidly coupled to the orifice (147), and have a maximum width, $d_{gap}$, between the outermost streamline (156) of each vortex and its adjacent high shear interface (109). In one embodiment, $d_{gap}$ may be reduced when adjusting the flow rates to trap and re-circulate the samples (102). In another embodiment, $d_{gap}$ may be widened when adjusting the flow rates to release the samples (102) from the vortices (152) and into their respective outer stream (154) for encapsulation at the droplet shearing junction (145).

In some embodiments, $v_d$, $v_c$, or both may be adjusted such that a ratio of $v_d$ to $v_c$ reduces $d_{gap}$ to be less than half a diameter of the smallest-sized samples, thereby trapping, re-circulating, and accumulating the samples within the vortices, and further reducing a width of the orifice to prevent encapsulation. In other embodiments, for each group of similarly-sized samples, $v_d$, $v_c$, or both are adjusted such that the ratio of $v_d$ to $v_c$ increases $d_{gap}$ to be about ½-1.5 the diameter of said samples. Thus, only similarly-sized samples are released from the vortices while larger-sized solid samples remain trapped in the vortices, and the width of the orifice is increased to allow for encapsulation of one such sample in one droplet.

In one embodiment, the dispersed samples (102) may comprise a plurality of cells, particles, or a combination thereof having varying diameters. In a preferred embodiment, the size-sorting method described herein allows for the samples to be released from the vortices (152) into the outer streams (154) in groupings of smallest to largest diameter. In some embodiments, a single sample (102) is encapsulated in one droplet (104) as said droplet is formed at the droplet shearing junction (145) and released from the orifice (147) into the output channel (160).

In accordance with the various embodiments described herein, the microfluidic device (100) may comprise a first dispersed phase channel (114) comprising one of the flow streams (107) that form the dispersed phase fluid (106), and a second dispersed phase channel (116) comprising the other flow stream (107). The first and second dispersed phase channels (114, 116) can merge to form the combining channel (110). In other embodiments, the microfluidic device (100) may further comprise an aqueous phase channel (117) intersecting with the first and second dispersed phase channels (114, 116). The aqueous phase channel (117) may comprise aqueous phase fluid (118) that flows into the combining channel (110) such that the aqueous phase fluid (118) forms a laminar interface stream (119) between the two flow streams (107). In some embodiments, the portions of the first and second continuous phase channels intersect the combining channel (110) orthogonally.

Consistent with the various embodiments of the present invention, the flow in the microfluidic device may be pressure-driven. In one embodiment, the flow rates can be adjusted using a constant pressure source via high speed solenoid valves. The valves may be controlled by a custom-built lab view program. As used herein, the flow rate is equivalent to the fluid pressure or channel resistance. The flow rates may be adjusted to generate the vortices, or to modulate between trap and release modes by varying the ratio of $v_d$ to $v_c$ ($v_d/v_c$). Alternatively or in addition, the dispersed phase pressure to continuous phase pressure ratio ($\varphi$) may be modified to adjust between the various modes. The ratios for trapping and release changes can depend on diameter of the cell or particle diameter. To illustrate, for a 10 μm diameter particle or cell, $v_d/v_c$ for trapping may be about 0.2-0.25, and greater than 0.27 for release. In various embodiments, the flow rate of the continuous phase fluid streams can be about 2-10 times greater that the flow rate of the dispersed phase fluid stream.

Microfluidic droplet generators utilizing the droplet generation method discussed above can be used to compartmentalize or encapsulate a single cell or a bead comprising single cell, cellular material or some other biological material in a single water droplet. Droplets encapsulating a single cell or bead can be useful for single cell assays of cells (e.g., cancer cells or immune cells) that exhibit biological heterogeneity for which assays that provide a population average may be insufficient. Encapsulation of a single cell (one cell) and/or a single bead (one-bead) in a single droplet can be useful for high-throughput screening of single cell. However, the efficiency of encapsulating a single cell (one cell) and/or a single bead (one-bead) in a single droplet can be as low as 0.1%, i.e. 1 in 1000 droplets may have a single cell (one cell) and/or a single bead (one-bead) while the remaining droplets may have no cells and/or beads or have more than one cell and/or one bead. This application contemplates a passive, hydrodynamic technique that can trap cells and/or beads in a plurality of independent vortices (e.g., two vortices) and then releasing the trapped cells and/or beads such that they are encapsulated in droplets. The size of the generated droplets can be adjusted to increase the probability that a single cell and/or bead is encapsulated in a single droplet. The droplet encapsulation efficiency can be increased to 30% or higher using the system and methods described herein, which could significantly improve the biomolecular capture efficiency various bead based single cell assays.

In various embodiments, the width of the various microfluidic channels (e.g., the first and second dispersed phase and aqueous phase channels (114, 116, 117); the combining channel (110); and the continuous phase channels (120, 130)) can range from about 25 µm to about 75 µm. For examples, the width of the various microfluidic channels can be in a range between about 30 µm to about 60 µm. Restricting the height of the various microfluidic channels to be less than twice the diameter of the solid samples can advantageously reduce the chance that the solid samples roll over each other and/or stack over each other.

In other embodiments, a width and/or length of the intersection region can be about 3-6 times the width of the various microfluidic channels (e.g., the combining channel, the first continuous phase channel, or the second continuous phase channel). For example, the width of the intersection region may be about 150 µm, which is about three times the width of a 50 µm incoming microfluidic channel. In another embodiment, the length of the intersection region may be about 200 µm, which is about four times the width of a 50 µm incoming microfluidic channels.

In some embodiments, the width of the orifice may be about 5-40 µm. For example, in one embodiments, the width of the orifice may be about 5-15 µm, about 10-20 µm, about 20-30 µm, or about 30-40 µm. In other embodiments, the width of the output channel may widen from the width of the orifice to a maximum width. The maximum width of the output channel can be about 2-10 times the width of the orifice. For examples, for a 30 µm orifice, the output channel widens from a minimum width of 30 µm to a maximum width of about 120 µm. In further embodiments, the width of the output channel may be reduced after reaching its maximum.

The device may be operated in a trapping mode in which the cells and/or beads introduced through the first and the second incoming microfluidic channels are trapped in independent vortices generated in the intersection region, as shown in FIG. 1A. The device may also be operated in a release/encapsulation mode in which the cells and/or beads trapped in the independent vortices are released and encapsulated in droplets as shown in FIG. 1B. Without relying on a particular theory, vortices can be generated when the ratio ($\varphi$) of fluid pressure between the dispersed phase (DP) and continuous phase (CP) is in a range between about 0.7 and 0.05. The range of values for $\varphi$ over which the device operates in the trapping mode and the range of values for $\varphi$ over which the device operates in the release/encapsulation mode can vary depending on the size of the beads/cells used. Experimentally, it was determined that trapping can occur when $\varphi$ is between about 0.05 and about 0.25 (e.g., about 0.15) for 10 micron polystyrene beads and k-562 cells. Experimentally, it was determined that release/encapsulation can occur when $\varphi$ is >0.25 and about 0.7 (e.g., about 0.5) for 10 micron polystyrene beads and k-562 cells.

In some embodiments, the velocities of the incoming flow streams (e.g. dispersed and continuous phase) can be adjusted such that laminar flow is established in the combining channel. For example, the flow rates of the incoming flow streams can be equal to each other to establish such laminar flow. By maintaining equal flow rates at inlets to the three incoming microfluidic channels, bead/cell migration across the streamlines due to Magnus force can be prevented. The flow streams in the combining channel can be separated by a laminar interface as a result of the laminar flow. In some embodiments, the constituents of the first solid sample (e.g., cells or cellular material) self-assemble on one side of the laminar interface and the constituents of the second solid sample (e.g., particles or beads) self-assemble on another side of the laminar interface. For example, as shown in the embodiment illustrated in FIG. 1, the beads or particles self-assemble in a single row along a channel wall of the combining channel and cells self-assemble in a single row along the opposite channel wall. The laminar flow comprising the dispersed phase fluid enters the intersection region.

In the intersection region, the flow rate of the continuous phase fluid flowing can be adjusted to create a high shear interface between the laminar flow and the continuous phase fluid stream. The size of the droplet can depend on the capillary number, $Ca=\mu V/\sigma$, where $\mu$ is the viscosity of the continuous phase comprising the second fluid, $V$ is the superficial velocity of the continuous phase comprising the second fluid, and $\sigma$ is the equilibrium surface tension between the continuous phase and the dispersed phase. In some embodiments, to generate droplets having an appropriate size to encapsulate a single cell and/or single bead, the capillary number can be in the range between about 0.01 and about 1 (e.g., about 0.1). In other embodiments, the droplet size can also be controlled by controlling the pressure ratio $\varphi$. In various embodiments, a droplet encapsulating a single cell and a single bead/particle can be achieved by controlling $\varphi$ to be between about 0.1 and about 0.5 (e.g., about 0.3). Depending on the pressure ratio and/or concentration of the solid samples, the generated droplets can have a size between about 20 microns and about 150 microns.

As discussed above, FIG. 2B shows the device operating in the trapping mode. In the trapping mode, flow parameters (e.g., flow velocity and/or fluid pressure) of the continuous and/or the dispersed phase can be adjusted to generate vortices (e.g., two independent vortices) in the intersection region to trap the cells and/or particles/beads introduced through the combining channel. Trapping and release of the cells and/or particles/beads depend on the distance ($d_{gap}$) between the interface of the continuous and the dispersed phase and the outermost streamline of the vortices. The $d_{gap}$ can depend on the flow velocities of the continuous and the dispersed phases. When the radius of cells and/or particles/beads is greater than $d_{gap}$, the center of the cells and/or particles/beads can cross into a closed streamline (e.g., a streamline of the vortex) thereby increasing the probability that the particles or cells are trapped. However, when the radius of particles or cells is less than $d_{gap}$, some cells and/or particles/beads may be trapped for some time in the vortices due to inertia or some other forces, but these cells and/or particles/beads may eventually be released from the vortices and pass through the orifice. Thus by adjusting $d_{gap}$, cells and/or particles/beads of different sizes can be trapped in the vortices.

When the concentration of the samples in the dispersed phase fluid is low, the microfluidic device can be operated in the trapping mode to increase the concentration of the sample prior to encapsulation in droplets. This can be advantageous in achieving high encapsulation efficiency and through-put. For example, in some embodiments, to get high concentration of cells in the dispersed phase, the flow parameters (e.g., flow velocity and/or pressure of the continuous and the dispersed phases) can be adjusted using the fluid controller to generate vortices such that $d_{gap}$ is less than the size (e.g., radius) of the cells so that all the particles or cells can be trapped in the vortices generated in the intersection region. The fluid controller can then be configured to release the trapped cells such that they are encapsulated in droplets within a short time interval (e.g., in less than 1 second).

Without wishing to limit the present invention, the encapsulation efficiency achieved using the methods described herein can be 30% or higher. More preferably, the encapsulation efficiency achieved using the methods described herein can be 50% or higher.

EXAMPLES

The following are non-limiting examples of implementing the trap and release mechanism of the present invention. It is to be understood that the examples are for illustrative purposes only and are not intended to limit the present invention in any way. Equivalents or substitutes are within the scope of the invention.

Materials and Methods

Microfluidic Device Preparation

To characterize the capillary migration of the droplets, microfluidic devices were fabricated in polydimethylsiloxane (PDMS) using soft lithography. The PDMS molded imprints and another plain PDMS layer were plasma treated for 2 minutes and were brought together to form a permanent seal. The device was left in the oven at 120° C. overnight to regain its natural hydrophobicity.

Fluidic Set-Up, Bead/Cell Preparation and Imaging

Ethyl oleate and 2% ABIL EM 90 form the continuous phase, and a mixture of water, lipids, glycerols and surfactant serves as the dispersed phase. Briefly, 5 mg DSPC (1,2-distearoyl-sn-glycero-3-phosphocholine) and 1.96 mg DSPE-PEG2000 (1,2-distearoyl-sn-glycero-3-phosphoethanolamine-N-[methoxy-(polyethyleneglycol)-2000]) were combined in a glass vial and dissolved in chloroform to form a homogeneous mixture. The solvent was evaporated with a nitrogen stream. 4 mL of ultra-pure water was added to the dry lipid mixture and sonicated at 50° C. for 20 minutes. The solution was combined with an additional 4 mL of glycerol and 2 mL of nonionic surfactant (Pluronic F-68), and then sonicated at 50° C. for 20 minutes. The lipid solution was sonicated again for 15 minutes immediately prior to use to minimize unwanted liposome formation.

The K-562 cells (American Type Culture Collection (ATCC®)) were cultured in a T-75 cell culture flask using RPMI 1640 as the basal medium to which fetal bovine serum (FBS) was added (10% by volume). The cell culture media is changed every three days until the cells proliferate to the desired confluency. The medium containing the cells was then transferred to a 10 mL Eppendorf tube, centrifuged at 1000 rpm for 5 min and the pellet was re-suspended in the freshly prepared aqueous/dispersed phase. The cell concentration in the resulting suspension was determined using an automated cell counter and appropriately diluted to the desired concentration. Similarly, the stock solution containing the beads was centrifuged at 3000 rpm; the supernatant was removed and the beads re-suspended in the freshly prepared aqueous phase. For demonstrating blood cell separation, normal donor blood was obtained from the Institute for Clinical and Translational Science (ICTS) at the University of California-Irvine under SPID protocol #6956, with Institutional Review Board (IRB) approval. The blood sample was diluted 10× using 1× phosphate buffered saline (PBS) prior to the experiments. The blood solution was stained using DAPI (4',6-diamidino-2-phenylindole, dihydrochloride) for the visualization of trapped WBCs in the vortices.

Both the continuous phase and the dispersed phase are introduced into the microfluidic chip using a constant pressure source via high speed solenoid valves controlled by a custom-built lab view program. The trapping, 1-1 encapsulation and size selective capture were monitored using a Nikon 100-S inverted microscope and recorded using a Phantom camera V-310 (Vision Research). To analyze the videos frame by frame to yield the encapsulation data, ImageJ, a public domain java based image processing software program developed at the National Institutes of Health, was used.

Design and Principle of Operation

As shown in FIG. 1, the microfluidic device comprises an expansion flow-focusing droplet generation junction. The aqueous (dispersed) phase containing the cells was introduced into the center channel, and it was focused into a narrow orifice by symmetric co-flowing streams of the continuous phase. The high viscosity shear applied by the continuous phase on the dispersed phase creates two symmetric three-dimensionally confined hydrodynamic vortices in the dispersed phase at the flow focusing junction. The vortices are directed in such a way that it is forward-oriented at the periphery and reverse-oriented at the center. Although the bulk of the dispersed phase fluid recirculates in the vortices, the continuity equation dictates that the mass flow of liquid into the system should be equal to the mass flow out of the system, as shown in the equation below:

$$\int \frac{\partial \rho}{\partial t} dV + \sum_i (\rho_i A_i v_i)_{in} - \sum_i (\rho_i A_i v_i)_{out} = 0 \qquad (1)$$

where $\rho$ is the density, V is the control volume (flow focusing junction), $A_i$ is the inlet or outlet area of the control volume, and $v_i$ is the velocity of fluid flowing in and out of the control volume. In steady state, incompressible flow, Equation 1 simplifies to:

$$A_1 v_1 = A_2 v_2 \qquad (2)$$

where $A_1$, $v_1$, $A_2$, and $v_2$ are respectively the inlet area, inlet velocity, outlet area and outlet velocity.

The dispersed phase entering through the center channel inlet recirculates within the vortex and exits through $d_{gap}$ into the orifice as droplets, where $d_{gap}$ is the width separating the closed loop vortex streamlines from the oil-aqueous interface. Within this $d_{gap}$, aqueous (dispersed) phase streamlines pass through the orifice to form the droplets. The continuity equation for the dispersed phase is derived as:

$$w \cdot h \cdot v_d \alpha 2 \cdot d_{gap} \cdot h \cdot (v_d + v_c) \qquad (3)$$

where w is the width and h is the height of the center channel inlet, and $v_d$ and $v_c$ are respectively the average velocities of the dispersed phase and the continuous phase. Since $v_d \ll v_c$, equation (3) can be approximated as:

$$w \cdot h \cdot v_d \alpha 2 \cdot d_{gap} \cdot h \cdot v_c \quad (4)$$

$$d_{gap} \alpha \frac{w}{c}\left[\frac{v_d}{v_c}\right] \quad (5)$$

At a fixed channel width (w), $d_{gap}$ depends only on the ratio of the dispersed phase to continuous phase flow velocity. Therefore, the exquisite control over the $d_{gap}$ is easily achieved by precise tuning of the relative flow rates using syringe pumps (in the case of constant flow) or the relative pressure ratios using pressure pumps (in the case of constant pressure). To achieve a faster response, a constant pressure source was used to drive the fluid into the system using high speed solenoid valves controlled by a custom-built LabVIEW program.

Mechanism of Cell Trapping and Single Cell Encapsulation

Cell Trapping: If the radius of the cells is greater than $d_{gap}$, the cells will not enter the droplets, instead they recirculate within the vortex. Notably, at this $d_{gap}$, the diameter of the droplets is smaller than the size of the cells to be encapsulated. This is because $d_{gap}$ and the droplet diameter are positively correlated as both are functions of $v_d/v_c$, the ratio of dispersed to continuous flow rate.

Single Cell Encapsulation: If the radius of the cell is comparable to $d_{gap}$, the cells will readily enter the droplets 1:1 and the diameter of the droplet at this $d_{gap}$ is large enough to encapsulate one cell in it.

Multiple encapsulations: If the radius of the cell $<<d_{gap}$, two or more cells at a given time can readily enter the droplets resulting in multiple encapsulations. Switching between these regimes is done by precisely adjusting the dispersed to continuous phase pressure ratio.

Mechanism of Size-Selective Capture of Cells

By selecting $d_{gap}$, only the cells smaller or equal in radius to $d_{gap}$ pass through, whereas all the larger cells get trapped. By modulating $d_{gap}$ to match the radius of various cell sizes, this technique is used to realize the size-selective trapping of cells. The principle of operation can be demonstrated by selecting blood as the dispersed phase, since it is constituted of cells of different sizes. Blood cells can be categorized by three main cell types—platelets, red blood cells (RBCs) and white blood cells (WBCs). Under the trapping regime, the complete trapping of all blood cells occurs at the junction. This is because $d_{gap}$, under this regime is tuned to be smaller than the radius of the platelets, which is the smallest type of cell (approx. 1-1.5 µm in radius) in the sample volume. Increasing $d_{gap}$ to be greater than the radius of the platelets (but less than the radius of RBCs) enables the release of platelets into the droplets while RBCs and WBCs remain trapped in the vortices. When all the platelets are released, $d_{gap}$ is increased to the radius of RBCs, enabling the release of RBCs (approx. 2-3.5 µm radius) into the droplets while the WBCs (approx. 6-7.5 µm radius) continue to recirculate and are trapped within the micro-vortices. This technique can be used for sample processing for droplet based liquid biopsy applications.

Results

Cell/Bead Trapping and One-to-One Encapsulation in Droplets

Using 2.5 µm, 4 µm, 7.32 µm and 10 µm diameter polystyrene beads to model the single cell encapsulations, it has been demonstrated that the cell/bead trapping and 1-1 encapsulation can be achieved in both the dripping and jetting regimes. The transition between the regimes is dictated by the Capillary number, $Ca=\mu \cdot v/\sigma$, where µ is the viscosity, v is the velocity of the continuous phase, and σ is the interfacial tension between the two fluid phases. The capillary number can be altered by changing the dispersed to continuous phase pressure ratio (φ). In the dripping regime, which occurs at $Ca\sim10^{-1}$, interfacial tension and viscosity can predict the formation of droplets. The droplets are monodispersed, and droplet break-up occurs within a characteristic diameter of the channel orifice. Increasing the capillary number to $10^1$ changes the regime from dripping to jetting. In the jetting regime, the dispersed phase protrudes like a long jet and it extends far beyond the channel orifice. In both the dripping and jetting regimes, the bead/cell trapping is similar whereas the 1-1 encapsulation is different.

Without wishing to limit the present invention, the Capillary number can vary inversely with $d_{gap}$, thus from trapping to release where $d_{gap}$ increases, the capillary number can decrease. In some embodiments, the Ca number for trapping mode can range from 0.10-0.15. In other embodiments, the Ca number for release mode can range from 0.05-0.08. For example, the Ca number may be 0.12 for trapping mode and 0.06 for release.

Figure 9:
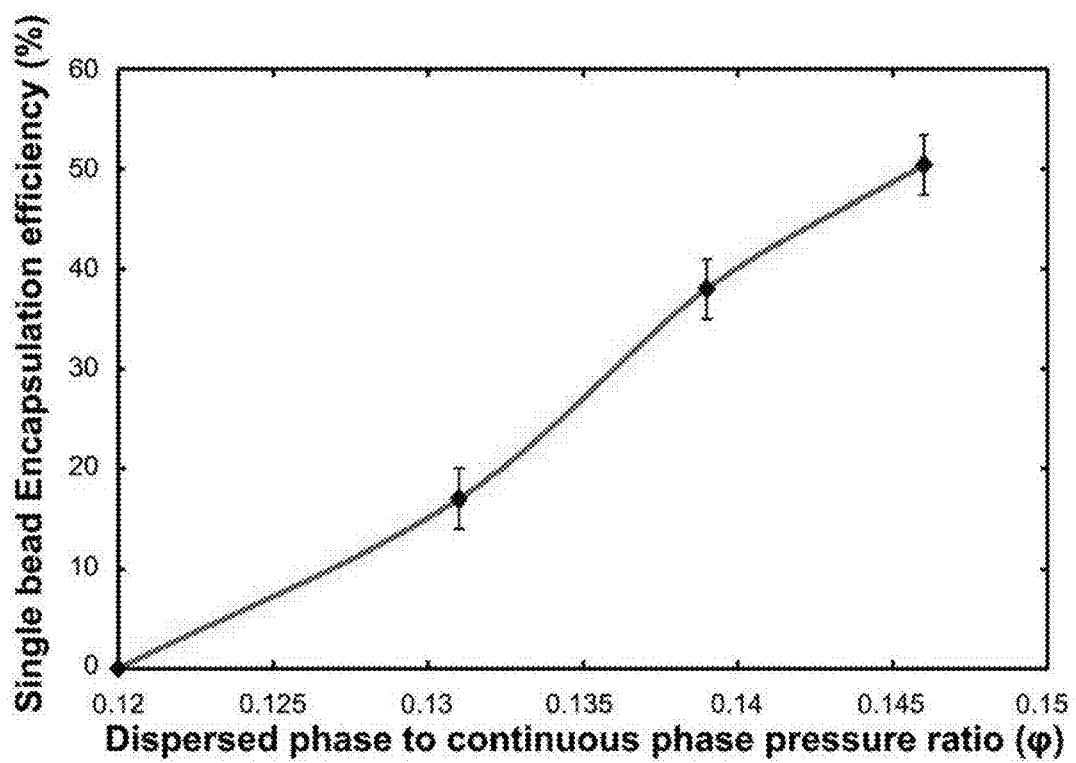
FIG. 9 is a graph of single bead encapsulation efficiency with respect to the dispersed to continuous phase pressure ratio. With 2.5 μm beads, the maximum single bead encapsulation efficiency is measured up to 50%.
Figure 10A:
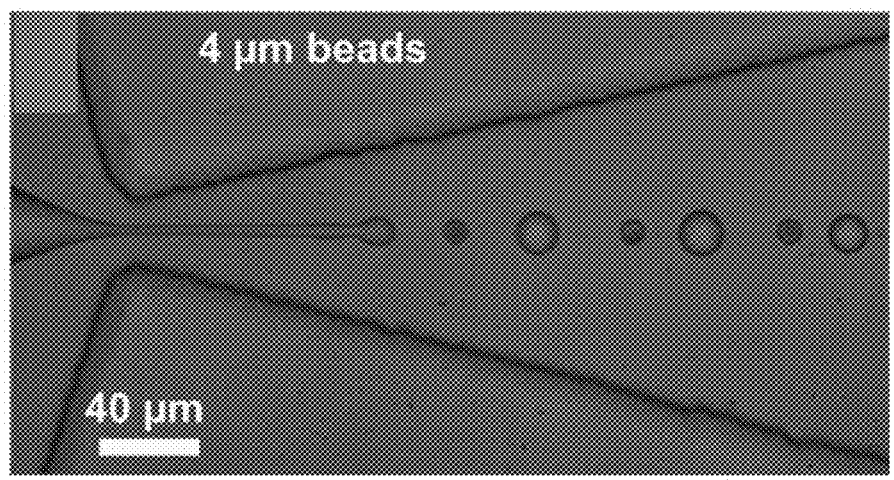
FIG. 10A shows single bead encapsulation of 4 μm beads in the jetting regime.
Figure 10B:
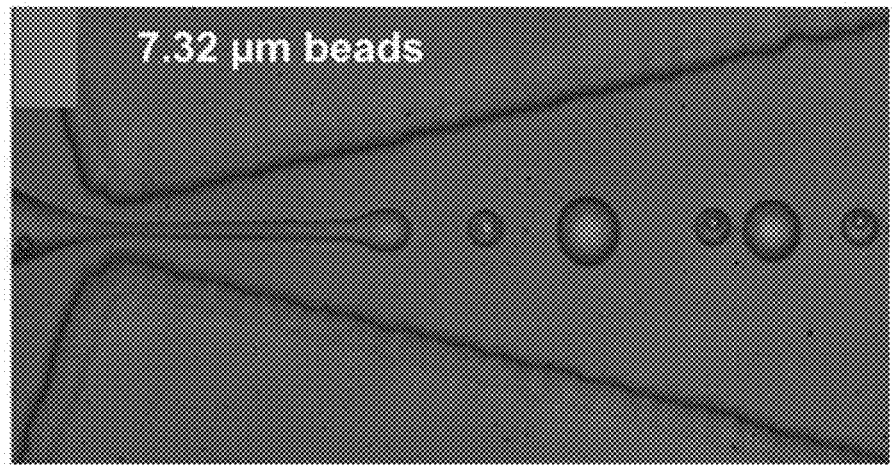
FIG. 10B shows single bead encapsulation of 7.32 μm beads in the jetting regime.
Figure 10C:
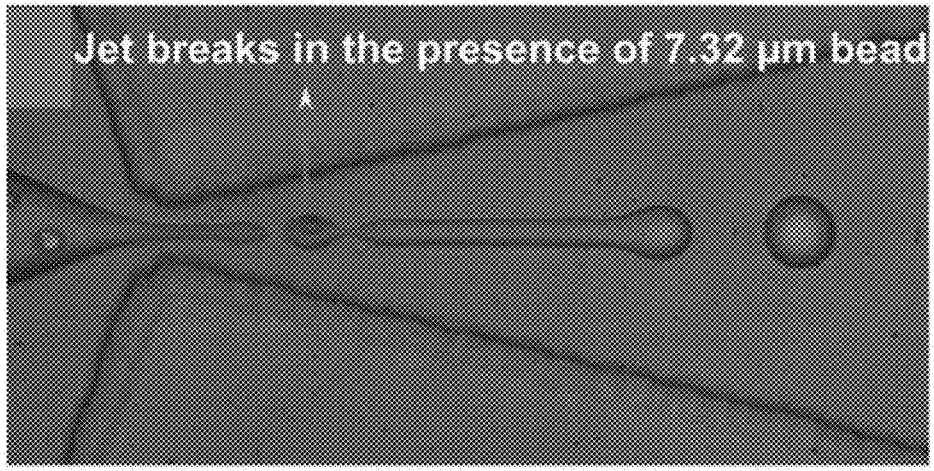
FIG. 10C shows a demonstration of the jet breaking scheme in the presence of 7.32 μm beads.

In the jetting regime, trapping and the one-to-one (1-1) encapsulation of 2.5 µm, 4 µm and 7.32 µm beads are illustrated in FIGS. 8A-8C, 9, and 10A-10C. One-to-one encapsulation is achieved by the Raleigh-Plateau instability jet break-up in the jetting regime. Beads enter the droplet based on $d_{gap}$ and the jet width. Tuning the jet width to be equal to the bead size ensures that no two beads enter the protruded jet stream at the same time. The beads upon entering the jet stream result in a jet break-up such that the bead-containing droplet will be smaller than the empty ones. It is also observed that the diameter of the droplets after encapsulation depends on the diameter of the beads encapsulated in it, which is evident from FIGS. 8B, 10A and 10B. This is because the larger beads (7.32 µm) require larger jet widths and occupy more space in the protruded jet stream than the smaller ones (2.5 µm) prior to the break-up. As shown in FIG. 9, the maximum 1-1 encapsulation efficiency for 2.5 µm beads is measured to be 50%. To ensure higher encapsulation efficiency, a size sorting scheme could be incorporated along with this technique.

Figure 11:
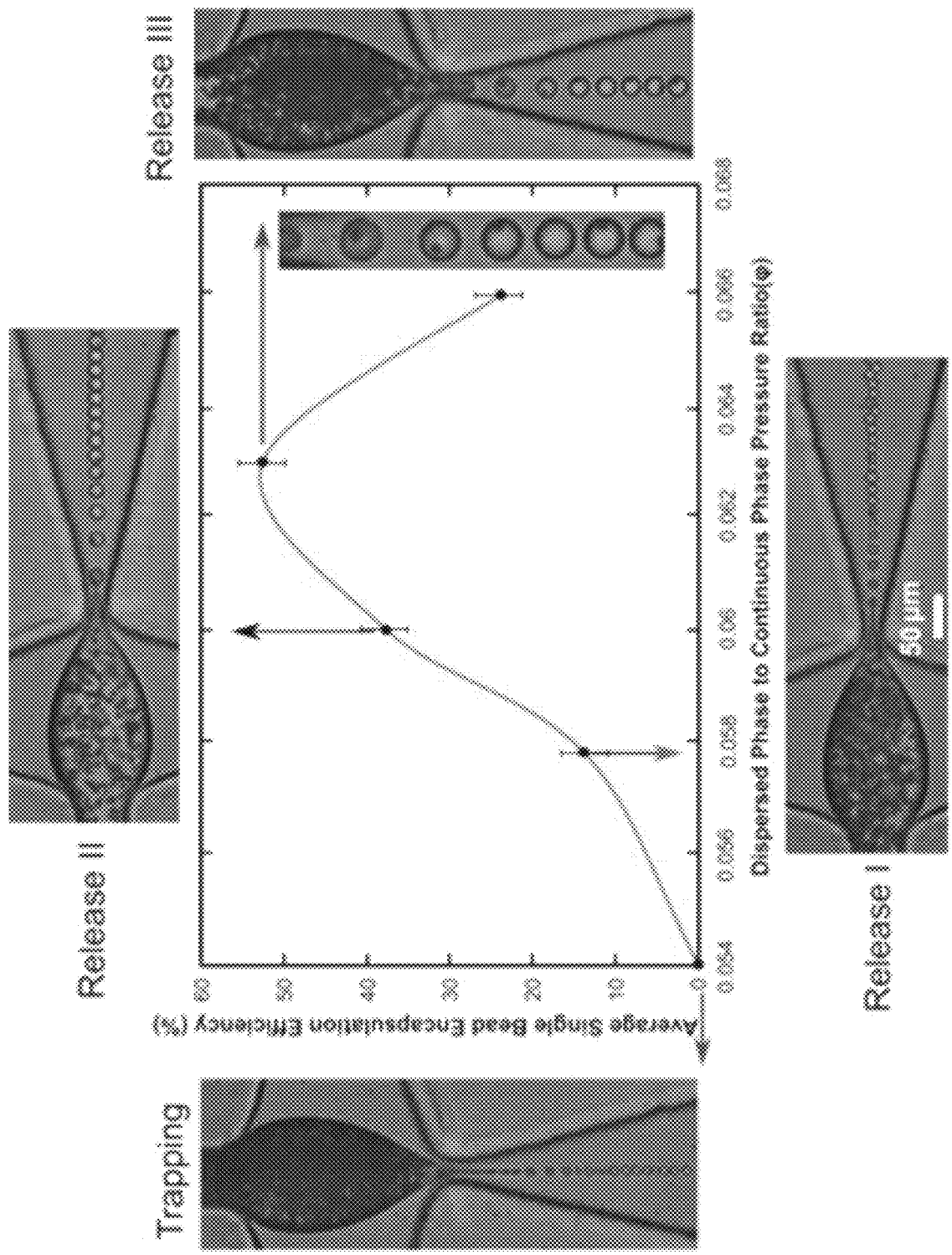
FIG. 11 shows single bead encapsulation in the dripping regime, including a graphical illustration of the average 1-1 encapsulation efficiency of 2.5 μm beads in the droplets. The insets are zoomed-in images corresponding to the maximum encapsulation efficiency. The encapsulation efficiency increases with the dispersed to continuous pressure ratio ($\varphi$), reaches a maximum, and decreases thereafter due to multiple bead encapsulations.
Figure 14:
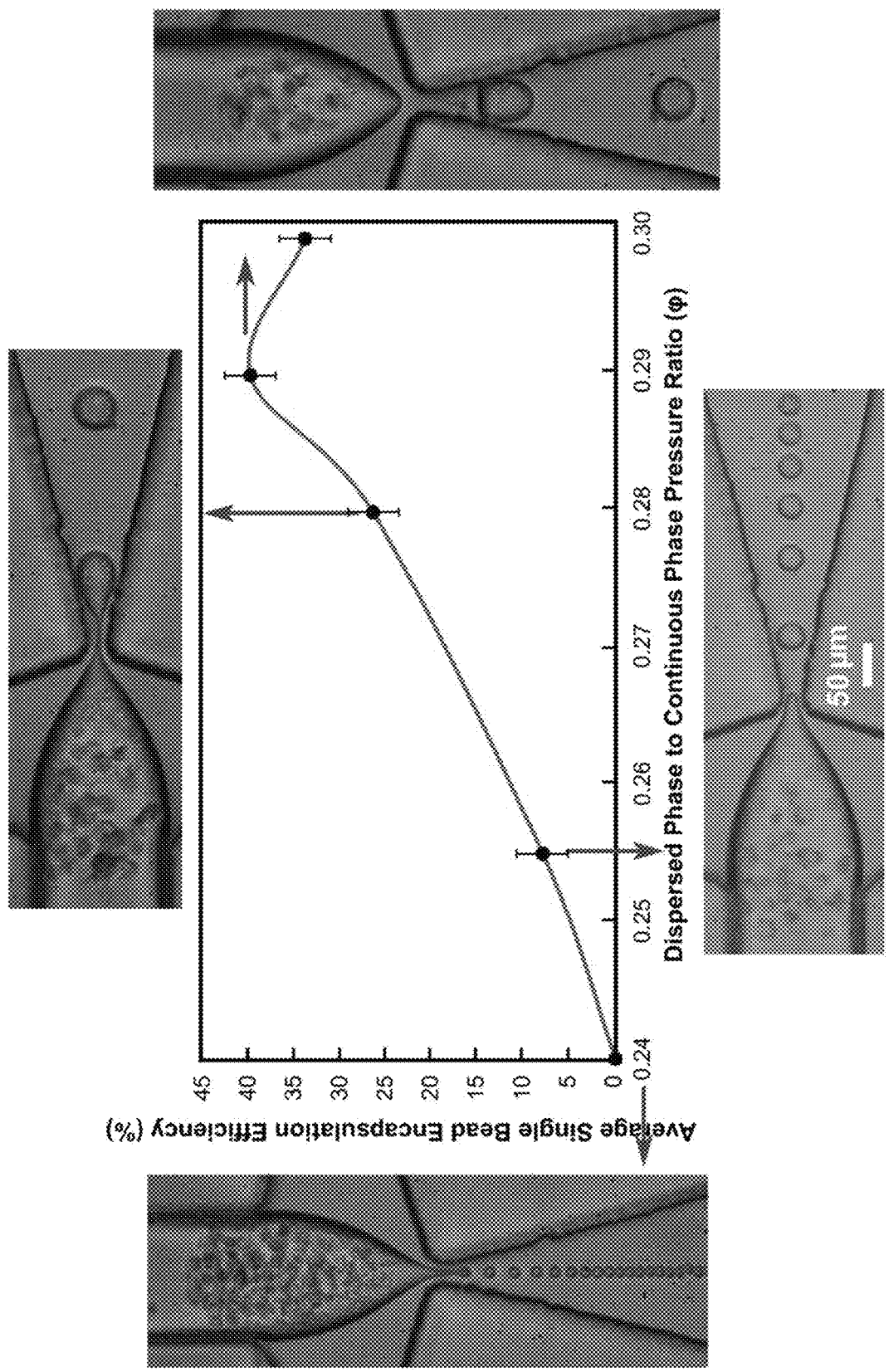
FIG. 14 shows a graph illustrating the 1-1 encapsulation efficiency of K-562 cells in the droplets. The insets are zoomed-in images corresponding to the maximum encapsulation efficiency. The encapsulation efficiency increases with the dispersed to continuous pressure ratio ($\varphi$), reaches a maximum, and decreases thereafter.

In the dripping regime, 2.5 µm, 7.32 µm and 10 µm diameter polystyrene beads are used as the models for 1-1 (one bead to one droplet) encapsulations. Tuning $d_{gap}$ to be comparable to the radius of each bead ensures 1-1 encapsulations. The dripping regime ensures that the encapsulated droplets are monodispersed. FIG. 11 illustrates the 1-1 encapsulation efficiency of the 2.5 µm beads. During the trapping mode, the dgap is not large enough to let the beads flow into the droplets. During the release mode, the 1-1 encapsulation efficiency increases with the dispersed to continuous phase pressure ratio (φ) because of the increase in $d_{gap}$. Since there exists a linear relationship between the droplet diameter and $d_{gap}$, it is evident that both the droplet diameter and $d_{gap}$ increase with the dispersed to continuous phase pressure ratio (φ). The 1-1 encapsulation efficiency reaches the maximum at an optimum $d_{gap}$, beyond which, it decreases due to multiple encapsulations. The maximum 1-1 encapsulation efficiency achieved using the 2.5 µm beads is around 50%. FIGS. 12A and 12B illustrates the trapping and 1-1 encapsulations of the 7.32 µm and 10 µm beads, respectively.

Referring to FIG. 14A, high-efficiency single cell encapsulation is achieved under the dripping regime using K-562 cell lines. In the trapping mode (achieved at low φ), the incoming cells will recirculate and are trapped within the micro-vortices, and this process continues until the whole expansion microfluidic junction is filled with cells. In the release mode, the single cell encapsulation efficiency increases with φ, however it decreases at a higher φ due to multiple encapsulations. Pressure optimizations for the trap and 1-1 release of different cells is determined by the size of the cells. Large size cells require a relatively greater $d_{gap}$ for the 1-1 encapsulation; hence the dispersed to continuous phase pressure ratio (φ) should increase accordingly and vice versa.

Referring to FIG. 13A-13B, compared to Poisson statistics, the present invention was able to achieve a >10× single cell encapsulation efficiency with the same cell concentration in the bulk solution. One of the significant features of this unique 'trap and release' mechanism is that it can perform high efficiency single cell encapsulations at very low cell loading densities (<2×10$^5$ cells per ml). This is because the cells are initially trapped in the micro-vortices, increasing the cell concentration locally before their encapsulation into the droplets. Additionally, this 'trap and release' technique is more efficient for low concentration samples as it also acts as an enrichment strategy. In the trapping mode, at a given cell concentration (4.8×10$^5$ cells per mL) and device dimensions (height ~100 μm), traps can get saturated in less than 20 seconds, approximately. The device continues to be functional even after saturating the trap. However, overcrowding of the cells in the trap may result in an occasional release of cells/beads into droplets due to hydrodynamic instability jet break-up. In the present configuration, instability occurred when the cell count in the vortex exceeded 120. This temporarily (<200 ms) disturbed the system before the process regained stability. At a higher cell concentration (2×10$^7$ cells per mL), saturation can much more quickly. Once the junction was saturated with cells, the mode from trapping to release was switched to avoid instability and ensure high efficiency of the 1-1 encapsulation.

Figure 17A:
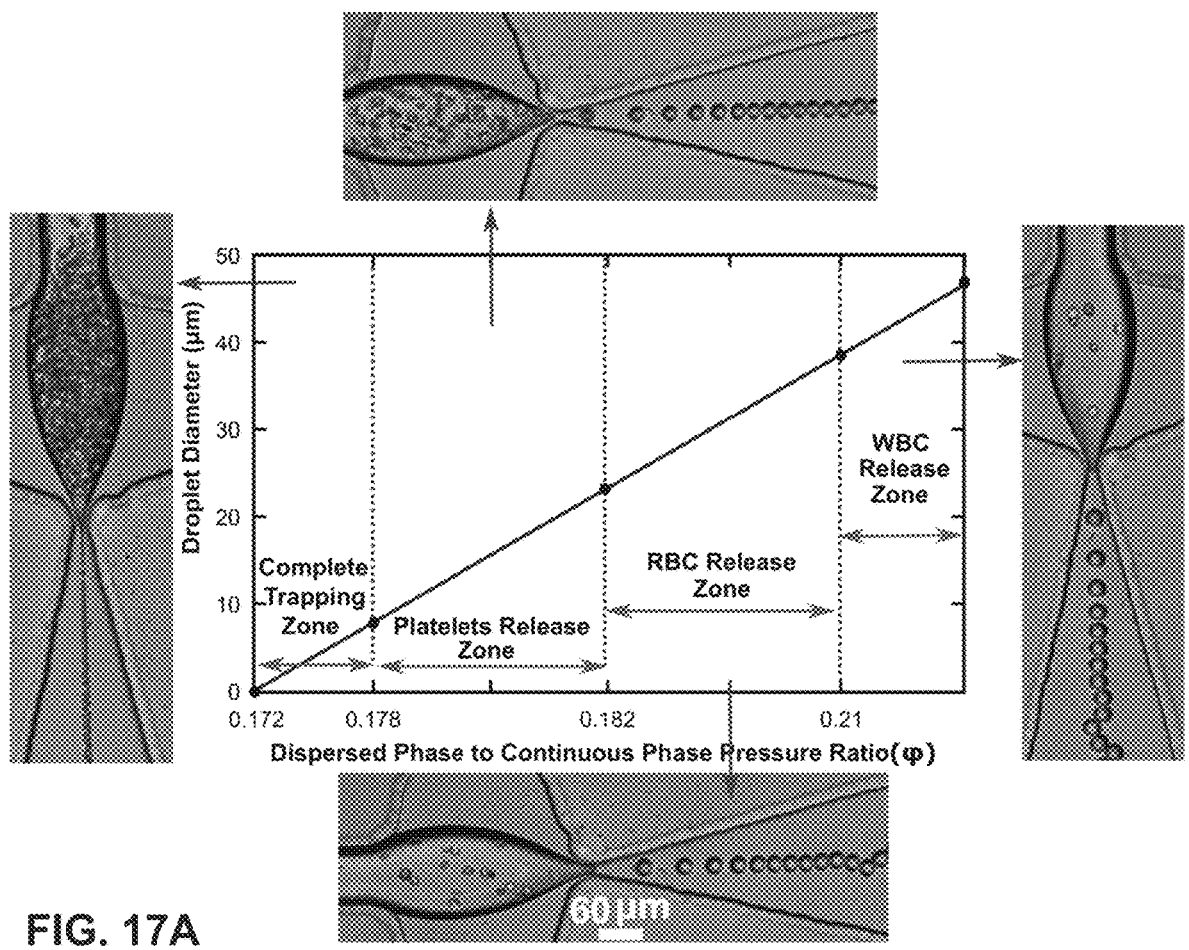
FIG. 17A is a graph of the trapping zone and distinct release zones for each cell type (platelets, RBCs and WBCs) based on their sizes plotted against the dispersed to continuous phase pressure ratio ($\varphi$). In the complete trapping zone, all the cells irrespective of their sizes are trapped in the micro-vortices. Under this regime, $d_{gap}$ is smaller than the radius of the smallest cell size. In the platelet release zone, only the platelets are released into the droplets while the RBCs and WBCs remain trapped in the micro-vortices. To capture large cells, including WBCs, $d_{gap}$ is tuned to be slightly smaller than the radius of the WBCs such that smaller sized cells including platelets and RBCs are encapsulated within the droplets trapping the WBCs in the micro-vortex.

The trap and release technique can be extended to perform size-selective sorting of cells from the sample. A 10× diluted blood sample was used to demonstrate this functionality. Initially, all the blood cells, including platelets (2-3 μm), RBCs (6-7 μm) and WBCs (12-15 μm), are trapped in the micro-vortices by tuning $d_{gap}$ to be smaller than the platelet radius. The size selective release of the cells is realized by increasing $d_{gap}$ such that the platelets are released first, followed by RBCs and finally WBCs. FIG. 17A illustrates the graphical experimental model for the trapping and distinct release regimes. In the complete trapping zone, all the blood cells are trapped in the micro-vortices. This is accomplished by tuning $d_{gap}$, to be smaller than the radius of the smallest cell in the sample. The platelet release regime allows only the platelets to be released into the droplets while the RBCs and WBCs recirculate within the vortices. The $d_{gap}$ at this zone is greater than the radius of the platelets but smaller than that of RBCs and WBCs. The RBC release zone is realized by tuning $d_{gap}$ to be greater than the RBC radius but smaller than that of WBCs so that the RBCs get released into the droplets while the WBCs remain trapped. While the WBC release regime starts, more than 90% of platelets and RBCs are filtered out from the trapped population.

Figure 17B:
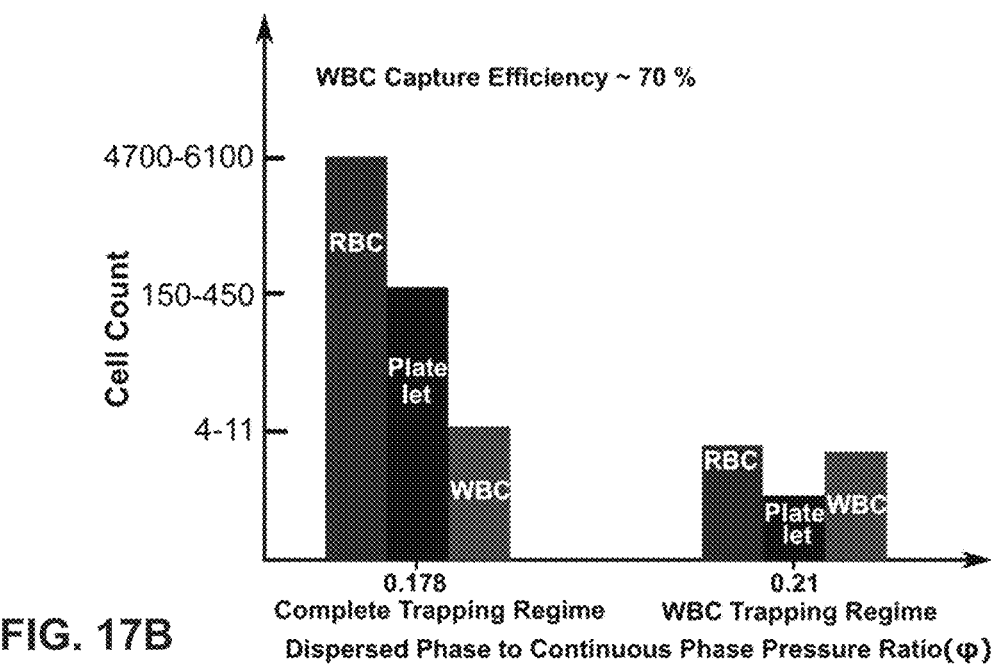
FIG. 17B is a quantitative estimate of the WBC capture efficiency. The present invention can achieve an efficiency of ~70%.
Figure 18A:
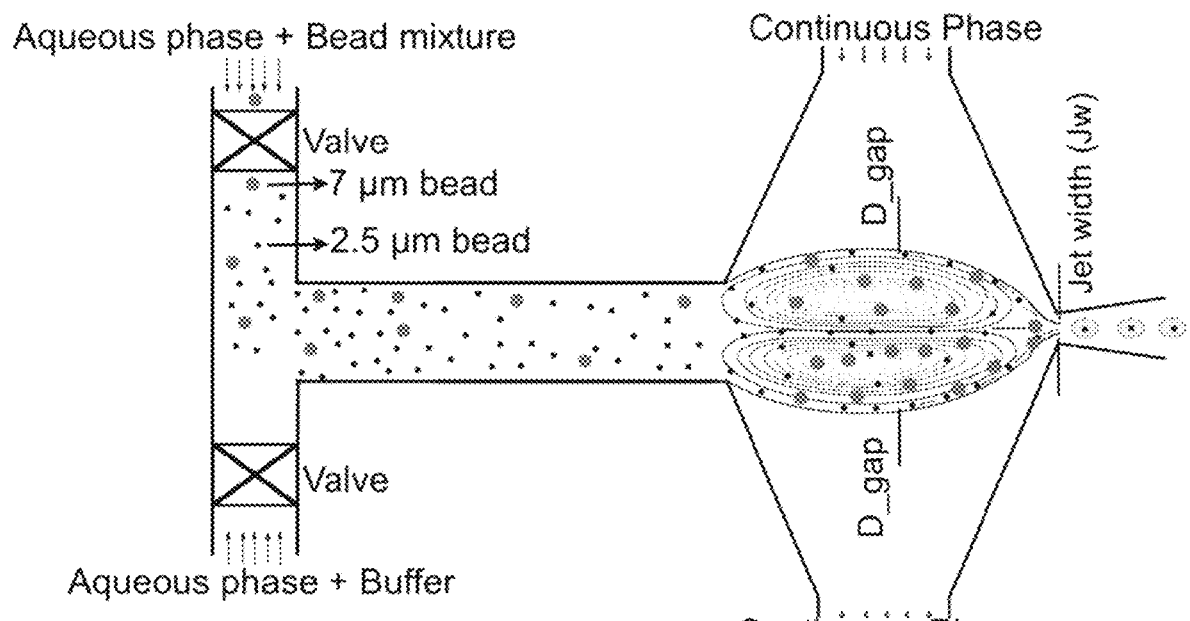
FIG. 18A is another embodiment of a single cell encapsulation schematic of size selective capture and release of beads.
Figure 18B:
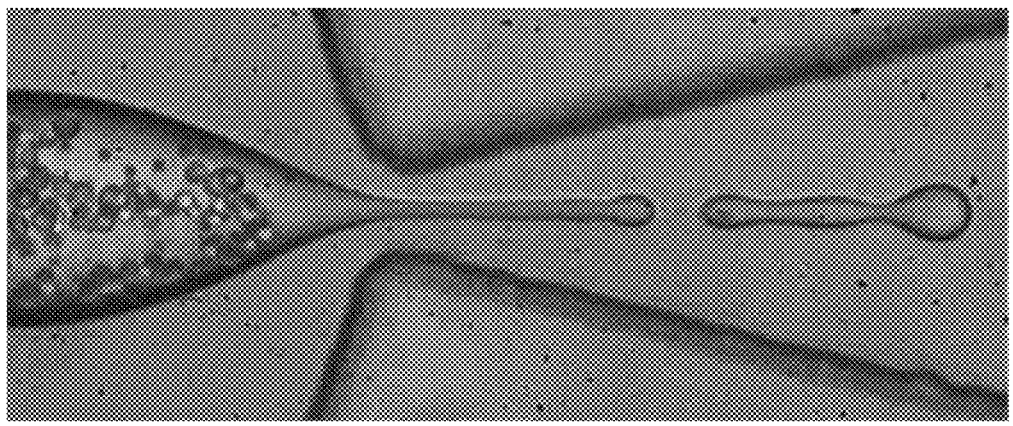
FIG. 18B shows trapping of 7.32 μm and 2.5 μm beads in the vortices. The $d_{gap}$ can be exquisitely controlled by tuning the pressure ratio ($\varphi$).
Figure 18C:
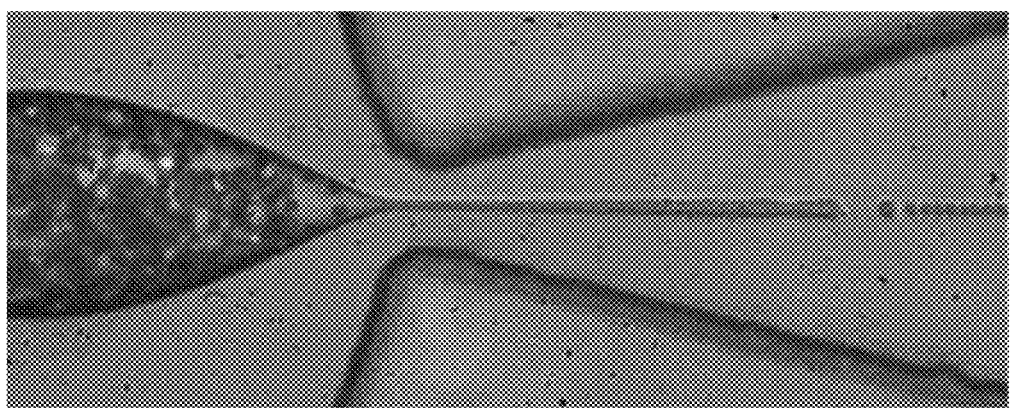
FIG. 18C shows release of 2.5 μm beads in droplet while the 7.32 μm beads are trapped.

Referring to FIG. 17B, the WBCs were successfully separated cells from the 10× PBS diluted blood sample at a 70% capture efficiency, which was determined from video counting using Image J software. As a control experiment, WBCs were DAPI stained to ensure fluorescence visualization, shown in FIG. 16A-16C. The range of the capture efficiency correlates with the range of WBC counts in the original sample. The advantage of this technique is that the cells can be collected in the micro-vortices and release them such that the smallest cells come out first followed by the next sized cells and so forth. This technique enables capturing the cells in the droplets based on their size from the sample population. These results could expand the capabilities of droplet microfluidic technology to address sample filtering and enrichment related to various sample processing stages in assays.

As used herein, the term "about" refers to plus or minus 10% of the referenced number.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. Reference numbers recited in the below claims are solely for ease of examination of this patent application, and are exemplary, and are not intended in any way to limit the scope of the claims to the particular features having the corresponding reference numbers in the drawings. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

What is claimed is:

1. A method for encapsulating a sample (102) in a droplet (104), said method comprising:
   a. providing a microfluidic device (100) comprising:
      i. a combining channel (110);
      ii. a first continuous phase channel (120) having a portion thereof disposed on one side of the combining channel;
      iii. a second continuous phase channel (130) having a portion thereof disposed on an opposite side of the combining channel, wherein said portions of the first and second continuous phase channels intersect at a terminal end of the combining channel to form an intersection region (140); and
      iv. an output channel (160) fluidly coupled to the intersection region (140);
   b. flowing a dispersed phase fluid (106) through the combining channel (110) at a first flow rate ($v_d$), wherein the dispersed phase fluid (106) comprises at least two flow streams (107), wherein one or both of said flow streams (107) comprises dispersed samples (102);
   c. co-flowing a continuous phase fluid (108) through each of the first and second continuous phase channels (120, 130) at a second flow rate ($v_c$), wherein the continuous phase fluid (108) intersect the dispersed phase fluid (106) at the intersection region (140), wherein a droplet shearing junction (145) is formed within the intersection region (140) as the continuous phase fluid (108) merges with the dispersed phase fluid (106), wherein the droplet shearing junction (145) comprises an orifice (147) fluidly coupling the output channel (160) to the intersection region (140);

d. adjusting $v_d$, $v_c$, or both such that the continuous phase fluid (108) forms a high shear interface (109) with the dispersed phase fluid (106) at the intersection region (140);

e. adjusting $v_d$, $v_c$, or both to generate a vortex region (150) in the dispersed phase fluid (106) at the intersection region (140), wherein the vortex region (150) comprises two vortices (152) each formed by one of the flow streams (107);

f. adjusting $v_d$, $v_c$, or both to trap and re-circulate the samples (102) within the vortices (152); and g. adjusting $v_d$, $v_c$, or both to release the samples (102) from the vortices (152) and generate droplets (104) encapsulating one sample (102) at the droplet shearing junction (145).

2. The method of claim 1, wherein each vortex (152) has an outer stream (154) disposed between an outermost streamline (156) of the vortex and the adjacent high shear interface (109), wherein each outer stream (154) is fluidly coupled to the orifice (147), wherein each outer stream (154) has a maximum width, $d_{gap}$, between the outermost streamline (156) of each vortex and the adjacent high shear interface (109), wherein $d_{gap}$ is reduced when adjusting the flow rates to trap and re-circulate the samples (102), wherein $d_{gap}$ is widened when adjusting the flow rates to release the samples (102) from the vortices (152) and into their respective outer stream (154) for encapsulation at the droplet shearing junction (145).

3. The method of claim 2, wherein $v_d$, $v_c$, or both are adjusted such that a ratio of $v_d$ to $v_c$ reduces $d_{gap}$ to be less than half a diameter of the samples, thereby trapping, re-circulating, and accumulating the samples (102) within the vortices (152), and further reducing a width of the orifice to prevent encapsulation, wherein $v_d$, $v_c$, or both are adjusted such that the ratio of $v_d$ to $v_c$ increases $d_{gap}$ to be about ½-1.5 the diameter of the samples, thereby releasing the samples from the vortices into the outer streams, and further increasing the width of the orifice to allow for encapsulation of a single sample in one droplet, or co-encapsulation of two different samples in one droplet.

4. The method of claim 1, wherein the microfluidic device (100) comprises a first dispersed phase channel (114) comprising one of the flow streams (107) forming the dispersed phase fluid (106), and a second dispersed phase channel (116) comprising the other flow stream (107), wherein the first and second dispersed phase channels (114, 116) merge to form the combining channel.

5. The method of claim 4, wherein the microfluidic device (100) further comprises an aqueous phase channel (117) intersecting with the first and second dispersed phase channels (114, 116), wherein the aqueous phase channel (117) comprises aqueous phase fluid (118), wherein the aqueous phase fluid (118) flows in the combining channel (110) such that the aqueous phase fluid (118) forms a laminar interface stream (119) between the two flow streams (107).

6. The method of claim 1, wherein the dispersed samples (102) comprises a plurality of cells flowing in one flow stream (107), and a plurality of particles flowing in the other flow stream (107), wherein at the intersection region (140), the cells are disposed in one vortex (152a) and the particles are disposed in the other vortex (152b), wherein when adjusting the flow rate for release, one cell is released from its vortex (152a) into its outermost stream (154a) and one particle is released from its vortex (152b) into its outermost stream (154b), wherein the one cell and the one particle are co-encapsulated in the one droplet (104) as said droplet is formed at the droplet shearing junction (140), wherein the droplet (104) co-encapsulating the one cell and one particle is released from the orifice (147) into the output channel (160).

7. The method of claim 1, wherein the dispersed samples (102) are either cells or particles, wherein one sample (102) is encapsulated as the droplet (104) is formed at the droplet shearing junction (140), wherein the droplet (104) encapsulating the one sample (102) is released from the orifice (147) into the output channel (160).

8. The method of claim 1, wherein the width of any of the microfluidic channels ranges from about 30 µm to about 60 µm.

9. The method of claim 8, wherein a length and a width of the intersection region are each about 3 to 5 times the width of any of the microfluidic channels.

10. A method for size-selective sorting and encapsulation of a solid sample (102) in a droplet (104), said method comprising:

a. providing a microfluidic device (100) comprising:
   i. a combining channel (110);
   ii. a first continuous phase channel (120) having a portion thereof disposed on one side of the combining channel;
   iii. a second continuous phase channel (130) having a portion thereof disposed on an opposite side of the combining channel, wherein said portions of the first and second continuous phase channels intersect at a terminal end of the combining channel to form an intersection region (140); and
   i. an output channel (160) fluidly coupled to the intersection region (140);

b. flowing a dispersed phase fluid (106) through the combining channel (110) at a first flow rate ($v_d$), wherein the dispersed phase fluid (106) comprises at least two flow streams (107), wherein one or both of said flow streams (107) comprises dispersed samples (102) having varying sizes;

c. co-flowing a continuous phase fluid (108) through each of the first and second continuous phase channels (120, 130) at a second flow rate ($v_c$), wherein the continuous phase fluid (108) intersect the dispersed phase fluid (106) at the intersection region (140), wherein a droplet shearing junction (145) is formed within the intersection region (140) as the continuous phase fluid (108) merges with the dispersed phase fluid (106), wherein the droplet shearing junction (145) comprises an orifice (147) fluidly coupling the output channel (160) to the intersection region (140);

d. adjusting $v_d$, $v_c$, or both such that the continuous phase fluid (108) forms a high shear interface (109) with the dispersed phase fluid (106) at the intersection region (140);

e. adjusting $v_d$, $v_c$, or both to generate a vortex region (150) in the dispersed phase fluid (106) at the intersection region (140), wherein the vortex region (150) comprises two vortices (152) each formed by one of the flow streams (107);

f. adjusting $v_d$, $v_c$, or both to trap and re-circulate the samples (102) within the vortices (152);

g. adjusting $v_d$, $v_c$, or both to release samples (102) of smallest size from the vortices (152) and generate droplets (104) encapsulating one of said samples (102)

at the droplet shearing junction (145), wherein the larger-sized samples (102) remain trapped in the vortices (152); and h. repeatedly adjusting $v_d$, $v_c$, or both such that release of similarly-sized samples from the vortices (152) and droplet encapsulation of one such solid sample occur in groupings ordered from smaller-sized samples to largest-sized solid samples.

11. The method of claim 10, wherein each vortex (152) has an outer stream (154) disposed between an outermost streamline (156) of the vortex and the adjacent high shear interface (109), wherein each outer stream (154) is fluidly coupled to the orifice (147), wherein each outer stream (154) has a maximum width, $d_{gap}$, between the outermost streamline (156) of each vortex and its adjacent high shear interface (109), wherein $d_{gap}$ is reduced when adjusting the flow rates to trap and re-circulate the samples (102), wherein $d_{gap}$ is widened when adjusting the flow rates to release the samples (102) from the vortices (152) and into their respective outer stream (154) for encapsulation at the droplet shearing junction (145).

12. The method of claim 11, wherein $v_d$, $v_c$, or both are adjusted such that a ratio of $v_d$ to $v_c$ reduces $d_{gap}$ to be less than half a diameter of the smallest-sized samples, thereby trapping, re-circulating, and accumulating the samples within the vortices, and further reducing a width of the orifice to prevent encapsulation,
wherein for each group of similarly-sized samples, $v_d$, $v_c$, or both are adjusted such that the ratio of $v_d$ to $v_c$ increases $d_{gap}$ to be about ½-1.5 the diameter of said samples, thereby releasing only said samples from the vortices while larger-sized solid samples remain trapped in the vortices, wherein the width of the orifice is increased to allow for encapsulation of one such sample in one droplet.

13. The method of claim 10, wherein the microfluidic device (100) comprises a first dispersed phase channel (114) comprising one of the flow streams (107) forming the dispersed phase fluid (106), and a second dispersed phase channel (116) comprising the other flow stream (107), wherein the first and second dispersed phase channels (114, 116) merge to form the combining channel.

14. The method of claim 13, wherein the microfluidic device (100) further comprises an aqueous phase channel (117) intersecting with the first and second dispersed phase channels (114, 116), wherein the aqueous phase channel (117) comprises aqueous phase fluid (118), wherein the aqueous phase fluid (118) flows in the combining channel (110) such that the aqueous phase fluid (118) forms a laminar interface stream (119) between the two flow streams (107).

15. The method of claim 10, wherein the dispersed samples (102) comprise a plurality of cells, particles, or a combination thereof having varying diameters, wherein the samples are released in groupings of smallest to largest diameter from the vortices (152) into the outer streams (154) and a single sample (102) is encapsulated in one droplet (104) as said droplet is formed at the droplet shearing junction (145) and released from the orifice (147) into the output channel (160).

16. The method of claim 15, wherein the cells are animal cells, plant cells, algae cells, fungal cells, bacterial cells, or a combination thereof.

17. The method of claim 15, wherein the cells are protoplasts, pollen grains, microspores, or tetrads.

18. The method of claim 15, wherein the cells comprise red blood cells, white blood cells, and platelets.

19. The method of claim 15, wherein the particles are beads.

20. A microfluidic device (100) for encapsulating a sample (102) in a droplet (104), said microfluidic device (100) comprising:

a. a combining channel (110) having a dispersed phase fluid (106) flowing therein at a first flow rate ($v_d$), wherein the dispersed phase fluid (106) comprises at least two flow streams (107), wherein one or both of said flow streams (107) comprises dispersed samples (102);

b. a continuous phase channel network (120) having a continuous phase fluid (108) flowing therein at a second flow rate ($v_c$);

c. an intersection region (140) formed by the continuous phase channel network (120) intersecting a terminal end of the combining channel, wherein the continuous phase fluid (108) intersects the dispersed phase fluid (106) to form a high shear interface (109) with the dispersed phase fluid,
wherein the intersection region comprises i) a droplet shearing junction (145) formed as the continuous phase fluid (108) merges with the dispersed phase fluid (106), wherein the droplet shearing junction (145) comprises an orifice (147), and ii) a vortex region (150) comprising two vortices each formed by one of the flow streams (107);

d. an output channel (150) fluidly coupled to the intersection region (140) via the orifice (147); and e. a fluid flow controller (170) configured to perform operations comprising:
  i. adjusting $v_d$, $v_c$, or both to trap and re-circulate the samples (102) within the vortices (152); and
  ii. adjusting $v_d$, $v_c$, or both to release the samples (102) from the vortices (152) and generate droplets (104) encapsulating at least one sample (102) at the droplet shearing junction (145).

* * * * *